(12) United States Patent
Smith et al.

(10) Patent No.: US 10,814,088 B2
(45) Date of Patent: *Oct. 27, 2020

(54) VENT ARRANGEMENT FOR PATIENT INTERFACE

(71) Applicant: ResMed Pty Ltd, Bella Vista, New South Wales (AU)

(72) Inventors: Ian Malcolm Smith, Sydney (AU); Muditha Pradeep Dantanarayana, Sydney (AU); Michael Thomas Janiak, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/737,308

(22) Filed: Jan. 8, 2020

(65) Prior Publication Data

US 2020/0139065 A1 May 7, 2020

Related U.S. Application Data

(60) Continuation of application No. 15/423,172, filed on Feb. 2, 2017, now Pat. No. 10,549,059, which is a
(Continued)

(51) Int. Cl.
*A61M 16/00* (2006.01)
*A61M 16/06* (2006.01)
(Continued)

(52) U.S. Cl.
CPC .... *A61M 16/0683* (2013.01); *A61M 16/0057* (2013.01); *A61M 16/06* (2013.01);
(Continued)

(58) Field of Classification Search
CPC .......... A61M 16/0683; A61M 16/0057; A61M 16/06; A61M 16/0816; A61M 16/208;
(Continued)

(56) References Cited

U.S. PATENT DOCUMENTS

| 535,795 A | 3/1895 | Hall |
|---|---|---|
| 3,291,127 A | 12/1966 | Eimer et al. |

(Continued)

FOREIGN PATENT DOCUMENTS

| AU | 712236 | 4/1999 |
|---|---|---|
| EP | 0 697 225 A2 | 2/1996 |

OTHER PUBLICATIONS

Instruction Brochure for "E-Vent-N" Aug. 1997, © Dräger Medizintecnik GmbH, 2 pages.

(Continued)

*Primary Examiner* — Steven O Douglas
(74) *Attorney, Agent, or Firm* — Nixon & Vanderhye P.C.

(57) ABSTRACT

A vent assembly for use with a respiratory mask of the type used in CPAP treatment includes a porous disk portion that is attached to a biasing member such that the disk portion is maintained in a substantially sealed position against a main vent to minimize airflow through at least one side vent of the vent assembly. Debris build-up on the disk portion can cause the biasing member to deflect to provide an additional path for airflow through the at least one side vent. In another embodiment, the vent assembly can also include an anti-asphyxia feature to provide an airflow path from the environment to the user. An oxygen diverter valve may be disposed between the breathing apparatus flow generator and an oxygen injection port.

30 Claims, 18 Drawing Sheets

Related U.S. Application Data continuation of application No. 14/019,590, filed on Sep. 6, 2013, now Pat. No. 9,629,973, which is a continuation of application No. 13/405,503, filed on Feb. 27, 2012, now Pat. No. 8,528,562, which is a continuation of application No. 12/048,603, filed on Mar. 14, 2008, now Pat. No. 8,146,596, which is a division of application No. 10/870,549, filed on Jun. 18, 2004, now Pat. No. 7,559,326.

(60) Provisional application No. 60/479,188, filed on Jun. 18, 2003.

(51) Int. Cl.
*A61M 16/20* (2006.01)
*A61M 16/08* (2006.01)
*A61M 16/12* (2006.01)

(52) U.S. Cl.
CPC .... *A61M 16/0611* (2014.02); *A61M 16/0616* (2014.02); *A61M 16/0816* (2013.01); *A61M 16/0825* (2014.02); *A61M 16/208* (2013.01); *A61M 16/12* (2013.01); *A61M 2202/0208* (2013.01); *A61M 2202/0225* (2013.01); *A61M 2205/0216* (2013.01); *A61M 2205/42* (2013.01)

(58) Field of Classification Search
CPC .......... A61M 16/12; A61M 2202/0208; A61M 2205/42; A61M 16/0611; A61M 16/0616; A61M 16/0825; A61M 16/0067; A61M 2202/0225; A61M 2205/0216
See application file for complete search history.

(56) References Cited

U.S. PATENT DOCUMENTS

| | | |
|---|---|---|
| 3,435,839 A | 4/1969 | Elder |
| 3,518,989 A | 7/1970 | Seeler et al. |
| 3,850,171 A | 11/1974 | Ball et al. |
| 4,239,038 A | 12/1980 | Holmes |
| 4,258,710 A | 3/1981 | Reber |
| 4,266,540 A | 5/1981 | Panzik et al. |
| 4,457,330 A | 7/1984 | Fields |
| 4,501,271 A | 2/1985 | Clifton et al. |
| 4,622,964 A | 11/1986 | Flynn |
| 5,002,050 A | 3/1991 | McGinnis |
| 5,036,843 A | 8/1991 | Schreurs |
| 5,065,756 A | 11/1991 | Rapoport |
| 5,103,854 A | 4/1992 | Bailey et al. |
| 5,148,802 A | 9/1992 | Sanders et al. |
| 5,477,852 A | 12/1995 | Landis et al. |
| 5,560,354 A | 10/1996 | Berthon-Jones et al. |
| 5,584,288 A | 12/1996 | Baldwin |
| 5,657,752 A | 8/1997 | Landis et al. |
| 5,896,857 A | 4/1999 | Hely et al. |
| 5,937,851 A | 8/1999 | Serowski et al. |
| 6,112,746 A | 9/2000 | Kwok et al. |
| 6,119,693 A | 9/2000 | Kwok et al. |
| 6,189,532 B1 | 2/2001 | Hely et al. |
| 6,192,886 B1 | 2/2001 | Rudolph |
| 6,561,190 B1 | 5/2003 | Kwok |
| 6,561,191 B1 | 5/2003 | Kwok |
| 6,581,594 B1 | 6/2003 | Drew et al. |
| 6,584,976 B2 | 7/2003 | Japuntich et al. |
| 6,638,357 B2 | 10/2003 | Mule'Stagno et al. |
| 7,063,086 B2 | 6/2006 | Shahbazpour et al. |
| 7,066,174 B1 | 6/2006 | Smith et al. |
| 7,559,326 B2 | 7/2009 | Smith et al. |
| 7,568,482 B2 | 8/2009 | Jaffre et al. |
| 8,146,596 B2 | 4/2012 | Smith et al. |
| 8,528,562 B2 | 9/2013 | Smith et al. |
| 2003/0066530 A1 | 4/2003 | Shahbazpour et al. |
| 2003/0164170 A1 | 9/2003 | Drew et al. |
| 2004/0255948 A1 | 12/2004 | Smith et al. |
| 2008/0156330 A1 | 7/2008 | Smith et al. |
| 2014/0000620 A1 | 1/2014 | Smith et al. |
| 2017/0143927 A1 | 5/2017 | Smith et al. |

OTHER PUBLICATIONS

U.S. Appl. No. 15/423,172, filed Feb. 2, 2017 for Oxygen Diverter Valve (parent application).

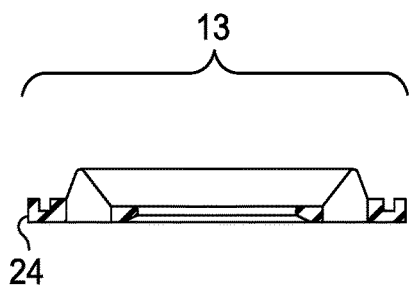
FIG. 18
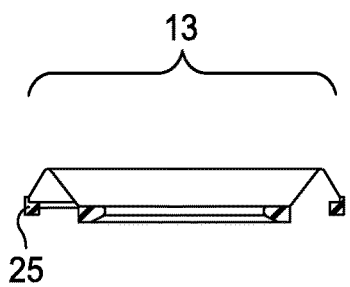
FIG. 19
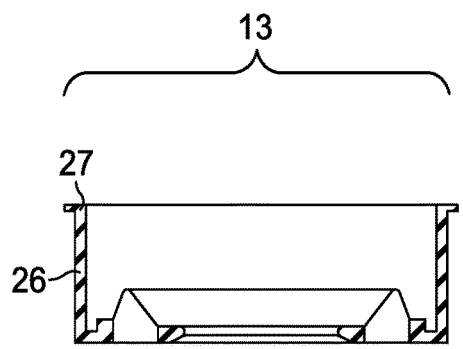
FIG. 20
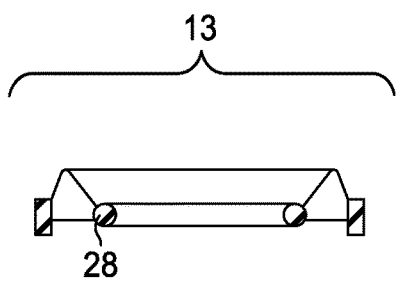
FIG. 21
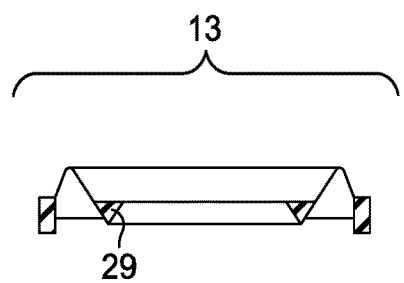
FIG. 22
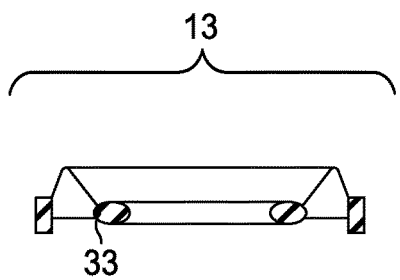
FIG. 21.1

VENT ARRANGEMENT FOR PATIENT INTERFACE

CROSS-REFERENCE TO RELATED APPLICATIONS

This application is a continuation of U.S. application Ser. No. 15/423,172, filed Feb. 2, 2017, which is a continuation of U.S. application Ser. No. 14/019,590, filed Sep. 6, 2013, now U.S. Pat. No. 9,629,973, which is a continuation of U.S. application Ser. No. 13/405,503, filed on Feb. 27, 2012, now U.S. Pat. No. 8,528,562, which is a continuation of U.S. application Ser. No. 12/048,603, filed Mar. 14, 2008, now U.S. Pat. No. 8,146,596, which is a divisional of U.S. application Ser. No. 10/870,549, filed Jun. 18, 2004, now U.S. Pat. No. 7,559,326, which claims the benefit of U.S. Provisional Application No. 60/479,188, filed Jun. 18, 2003, each incorporated herein by reference in its entirety.

BACKGROUND OF THE INVENTION

1. Field of the Invention

The invention generally relates to the field of treatment for breathing disorders. More specifically, the present invention relates to the vent of a respiratory mask for ventilatory treatment or assistance.

The present invention also relates to an oxygen diverter valve used in systems where air or another breathable gas is mixed with oxygen. The valve may be used in conjunction with the vent. The valve has been developed primarily for use between a gas delivery apparatus for delivery of breathable gas and an oxygen port. One goal is that that when airflow is stopped the valve closes and prevents oxygen to flow upstream into the flow generator.

The valve is also suitable for use in other gas delivery systems, such as those used in assisted respiration and Non-Invasive Positive Pressure Ventilation (NIPPV).

2. Background Information

The application of Continuous Positive Airway Pressure (CPAP) via a mask is a common ameliorative treatment for sleep disordered breathing (SDB), including obstructive sleep apnea (OSA). In CPAP treatment for OSA, air or other breathable gas is supplied to the entrance of a patient's airways at a pressure elevated above atmospheric pressure, typically in the range 3-20 cm $H_2O$ as measured in the patient interface. It is also known for the level of treatment pressure to vary during a period of treatment in accordance with patient need, that form of CPAP being known as automatically adjusting CPAP treatment.

Typically, the patient interface for CPAP treatment can include a nasal mask. The nasal mask is generally defined by a mask shell that forms an inner cavity defined by its interior surface, a mask cushion and the user's face, and a gas inlet. A swivel elbow may be coupled to the gas inlet, or the gas inlet may be attached directly to a conduit that supplies the air or breathable gas. Alternatively, a nose-mouth mask, full-face mask, nasal prongs or nasal pillows may be used. One example of a nasal mask is described in U.S. patent application Ser. No. 09/570,907, which is incorporated herein by reference in its entirety.

An apparatus including a mask should be quiet and comfortable to encourage patient compliance with therapy; however, exhausting exhaled air from a vent into the atmosphere may create noise. Because CPAP treatments are normally administered while the patient is sleeping, minimization of such noise is desirable for both the comfort of the patient and any bed partner. Accordingly, a need has developed in the art to overcome the deficiencies of prior art devices that may undesirably make noise.

The inventor has discovered that a vent with fine holes or a vent covered with a finely meshed porous material similar to Gore-Tex® may be used to produce a respiratory mask having low vent noise. However, the inventor identified two potential problems encountered by the use of the vent including fine holes or the vent covered with finely meshed material. The first problem may occur if the vents of the mask become blocked or clogged with debris. The blocked vents reduce airflow through the vents, which could cause a high level of $CO_2$ to accumulate in the mask and thereby create a safety concern to the user. The second problem may occur if the vents are manufactured with the intent of obtaining repeatable pressure flow characteristics, because it is difficult to consistently duplicate the vents of the mask at a precision required to get repeatable pressure flow characteristics.

Based upon the above, the inventor has identified a need for a vent that is quiet, comfortable, and constructed of a material that overcomes the problems of potential high $CO_2$ levels and permits consistent pressure-flow characteristics to be achieved.

SUMMARY OF THE INVENTION

Devices consistent with the principles of the present invention, as embodied and broadly described herein, overcome one or more of the difficulties indicated above and others by providing a device that utilizes a porous material having fine holes as vents to produce a respiratory mask having very low noise. Moreover, these features may be obtained while preventing the risk of high $CO_2$ levels and obtaining consistent pressure flow characteristics.

In one embodiment of the present invention, a vent assembly for a respiratory mask includes a main vent portion configured to permit gas to flow via a primary flow path through a mask shell to the environment when the respiratory mask is in use during a first predetermined condition of the vent assembly. A porous disk portion is configured to substantially seal against the main vent portion to provide the primary flow path through the main vent portion and the disk portion during the first predetermined condition of the vent assembly. A secondary vent portion is configured to provide a secondary flow path when a predetermined second condition of the vent assembly and flow pressure causes a predetermined deflection of the disk portion.

In another embodiment of the present invention, a vent assembly for a respiratory mask includes a main vent portion formed in a mask shell and configured to permit gas to flow via a primary flow path through the mask shell to the environment when the respiratory mask is in use during a first predetermined condition of the vent assembly. A flap portion includes a porous section and a flap insert wherein the flap portion is configured to substantially seal against the main vent portion to provide the primary flow path through the main vent portion and the porous section of the flap portion during the first predetermined condition of the vent assembly. The flap portion is further configured to develop a gap between the mask shell and the flap portion when a predetermined second condition of the vent assembly and flow pressure causes a predetermined deflection of the flap to provide a secondary flow path from the mask shell around the flap portion to the environment.

In yet another embodiment of the present invention, a vent assembly for a respiratory mask includes a main vent portion configured to permit gas to flow via a primary flow path through a mask shell to the environment when the respiratory mask is in use during a first predetermined condition of the vent assembly. A secondary vent portion is configured to provide a secondary flow path during a predetermined second condition of the vent assembly and flow pressure, wherein the predetermined second condition occurs when the main vent portion is blocked by a predetermined amount of debris.

The oxygen diverter valve is typically used in an airflow to which oxygen is added. The valve is typically placed between the flow generator and the oxygen injection point.

The valve preferably includes two cavities separated by a flap. The first (upstream) cavity is connected to the air supply. The second (downstream) cavity connects to the oxygen injection port. The downstream cavity is also open to the atmosphere via several closable vents. The flap which separates both cavities includes a mounting rim, a hinged flap section and a sealing section.

At rest, the flap is typically in a closed position, thereby preventing the gas from flowing upstream from the oxygen injection cavity into the air supply cavity. When the flap is in closed position the gas in the oxygen injection cavity can vent into the atmosphere.

When the relative air pressure in the air supply cavity exceeds a certain level the flap is forced open allowing the air to flow downstream from the air supply cavity into the oxygen injection cavity. The flap closes the vents to the atmosphere when open.

The operating threshold can be altered to suit particular applications. For example, a valve suitable for use in adult ventilatory assist therapy has an operating threshold of less than 2 cm $H_2O$.

Preferably, the housing includes two housing parts that are releasably engageable with one another. In an embodiment, the housing parts engage by way of clip style fittings. Preferably, the housing includes a gas inlet in the form of a female conical connector adapted to frictionally engage a flexible conduit in fluid communication with the gas delivery apparatus and a gas outlet in the form of a male conical connector adapted to engage an oxygen injection point or a flexible or rigid conduit in fluid communication with the mask.

Desirably also, one of the gas inlets or outlets includes a snap-engageable and detachable swivel portion adapted to engage the mask or flexible conduit. In a preferred embodiment, the inlet and outlet are respectively provided on one of the two housing parts.

In an embodiment, the housing includes several vents spaced about the periphery of the oxygen injection cavity.

The mounting ring of the flap preferably includes a rim which fits snugly into a receiving cavity in the housing. The mounting ring can have a square, round or tapered cross section.

In one preferred form, the flap is substantially round. In other forms, the flap can be full or part elliptical, rectangular or any other shape.

The housing is preferably manufactured from plastics material, for example polycarbonate (Bayer Makrolon 2458). The flap assembly is preferably manufactured from a flexible elastomeric material such as a silicone rubber (Dow Corning Silastic 94-595-HC).

In a further embodiment, the housing is of unitary construction.

BRIEF DESCRIPTION OF THE DRAWINGS

The above and other features and advantages of the present invention are further described in the detailed description which follows, with reference to the drawings, and by way of non-limiting exemplary embodiments of the present invention, wherein like reference numerals represent similar parts of the present invention throughout the several views and wherein:

FIG. 18 is a cross sectional view of an embodiment of a flap with a different rim;

FIG. 19 is a cross sectional view of another embodiment of a flap with a different rim;

FIG. 20 is a cross sectional view of yet another embodiment of a flap with a different rim;

FIG. 21 is a cross sectional view of another embodiment of a flap with a different toroid;

FIG. 21.1 is a cross sectional view of another embodiment of a flap with yet another toroid;

FIG. 22 is a cross sectional view of yet another embodiment of a flap with a different toroid;

DETAILED DESCRIPTION OF PREFERRED EMBODIMENTS

Figure 1A:
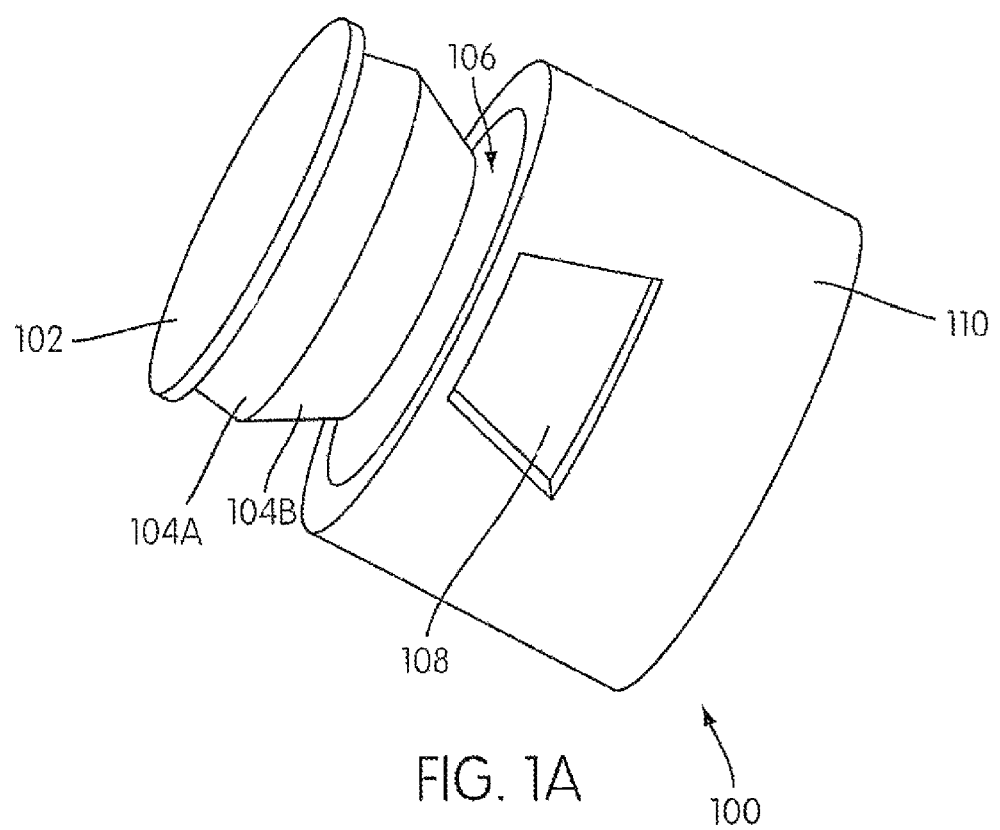
FIG. 1A illustrates an exploded view of a vent assembly of a respiratory mask in accordance with an embodiment of the present invention.

FIG. 1A illustrates an exploded view of a vent assembly 100 of a respiratory mask frame 110 in accordance with a first embodiment of the present invention. The mask frame 110 includes at least one side vent 108, a main vent 106, a bellows portion 104, and a disk portion 102 attached to an end of the bellows portion 104. Bellows portion 104 may be, for example, constructed from a silicone material or other suitable flexible material known in the art. The bellows portion 104 can have a first bellows section 104A and a second bellows section 104B constructed and arranged to provide a biasing force. Bellows portion 104 may also be substituted by a biasing member such as a spring that is assembled to the mask frame 110. Disk portion 102 may be, for example, a porous plate having multiple, finely-spaced holes and/or a piece of finely meshed fabric.

As illustrated in FIG. 1A, the disk portion 102 may be attached to the top of bellows portion 104 such that a biasing force produced by the bellows portion 104 maintains the disk portion 102 in a sealed position against an inside of the main vent 106 opening.

Figure 1B:
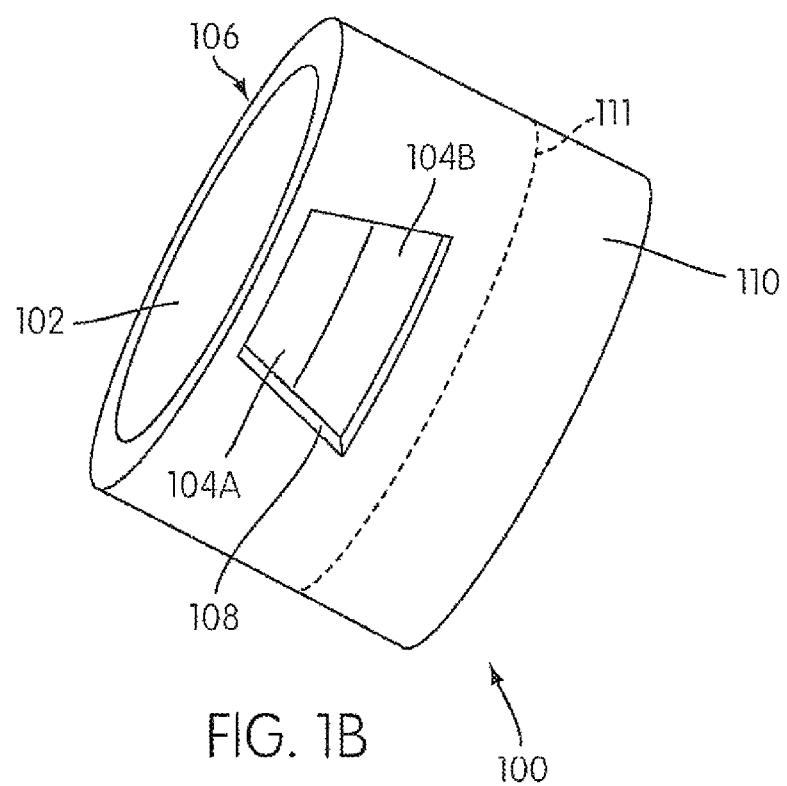
FIG. 1B illustrates a vent assembly of a respiratory mask in accordance with an embodiment of the present invention.

FIG. 1B illustrates the bellows portion 104 arranged within the mask housing 110 such that the disk portion 102 is flush with the main vent 106. A bellows stop 111 (illustrated in phantom) within the mask frame 110 can be arranged to support the bellows portion 104 or biasing member when the bellows portion 104 or biasing member and the disk portion 102 are assembled within the mask frame 110. Portions of the first bellows section 104A and the second bellows section 104B are visible through the side vent 108.

In use, a flow generator provides a constant positive pressure to the interior of the mask. Airflow caused by the positive pressure and/or air exhaled by the user is vented to the environment via the vent assembly 100. Preferably, the biasing force of the bellows portion 104 is greater than or equal to the force applied to the disk portion 102 by airflow pressure when the disk is in a clean condition and exposed to flow pressure during use. The sealed positioning of the disk portion 102 against the main vent 106 minimizes airflow through the side vent 108.

As an example of the function of the force applied to the disk portion 102 by flow pressure, the following is provided. A projected area of the disk portion 102 can be determined based upon an area of the disk portion 102 excluding the finely-spaced holes, passages or pores. For example, a disk portion 102 which is 50% porous and has an area of 10 mm$^2$ would have a projected area of 5 mm$^2$. The projected area is exposed to the flow pressure. The force applied by the flow pressure to the disk portion 102 can be calculated by multiplying the flow pressure with the projected area of the disk portion 102. When the disk portion 102 is in a clean condition, i.e., there is little or no debris build-up on the disk portion 102, the total projected area of the disk portion 102 that is exposed to the flow pressure is low. Accordingly, the force applied by the flow pressure to the disk portion 102 does not exceed the force applied in the opposite direction by the bellows portion 104 to the disk portion 102, and the bellows portion 104 is not significantly compressed. As such, air flows primarily through the holes or passages in the disk portion 102. Airflow is minimized through the side vent 108 because the disk portion 102 is not substantially displaced by the flow pressure and minimizes exposure of the side vent 108 to the primary airflow path.

However, when the disk portion 102 is in an unclean condition, i.e., when there is a build-up of debris on the disk portion 102, the total projected area of the disk portion 102 exposed to the flow pressure is increased by the debris build-up that blocks air flow through the holes or passages in the disk portion 102 and increases the total projected area. A proportional relationship can exist between the debris build-up on the disk portion 102 and the total projected area exposed to flow pressure, i.e., as the debris build-up increases, the total projected area exposed to the flow pressure increases. Accordingly, the force effectively applied to the disk portion 102 by the flow pressure increases.

The increase of force applied to the disk portion 102 can displace the disk portion 102 in the direction of flow pressure and can cause the bellows portion 104 to compress, providing a path for the airflow to bypass the disk portion 102 by permitting secondary airflow through side vent 108. The amount of secondary airflow through side vent 108 can be proportional to the amount of debris build-up on the disk portion 102 (depending at least upon the shape of the side vent 108 and the spring force provided by the bellows portion 104). The extra force applied to the disk portion 102 can be directly related to the increased projected area created by the debris build-up, i.e., as the blocked area of the disk portion 102 increases, the force applied to the bellows portion 104 also increases. Preferably, the vent assembly 100 is configured and arranged such that, regardless of the debris build-up and associated displacement of the disk portion 102, total combined airflow through the main vent 106 and the side vent 108 remains substantially constant.

Figure 2:
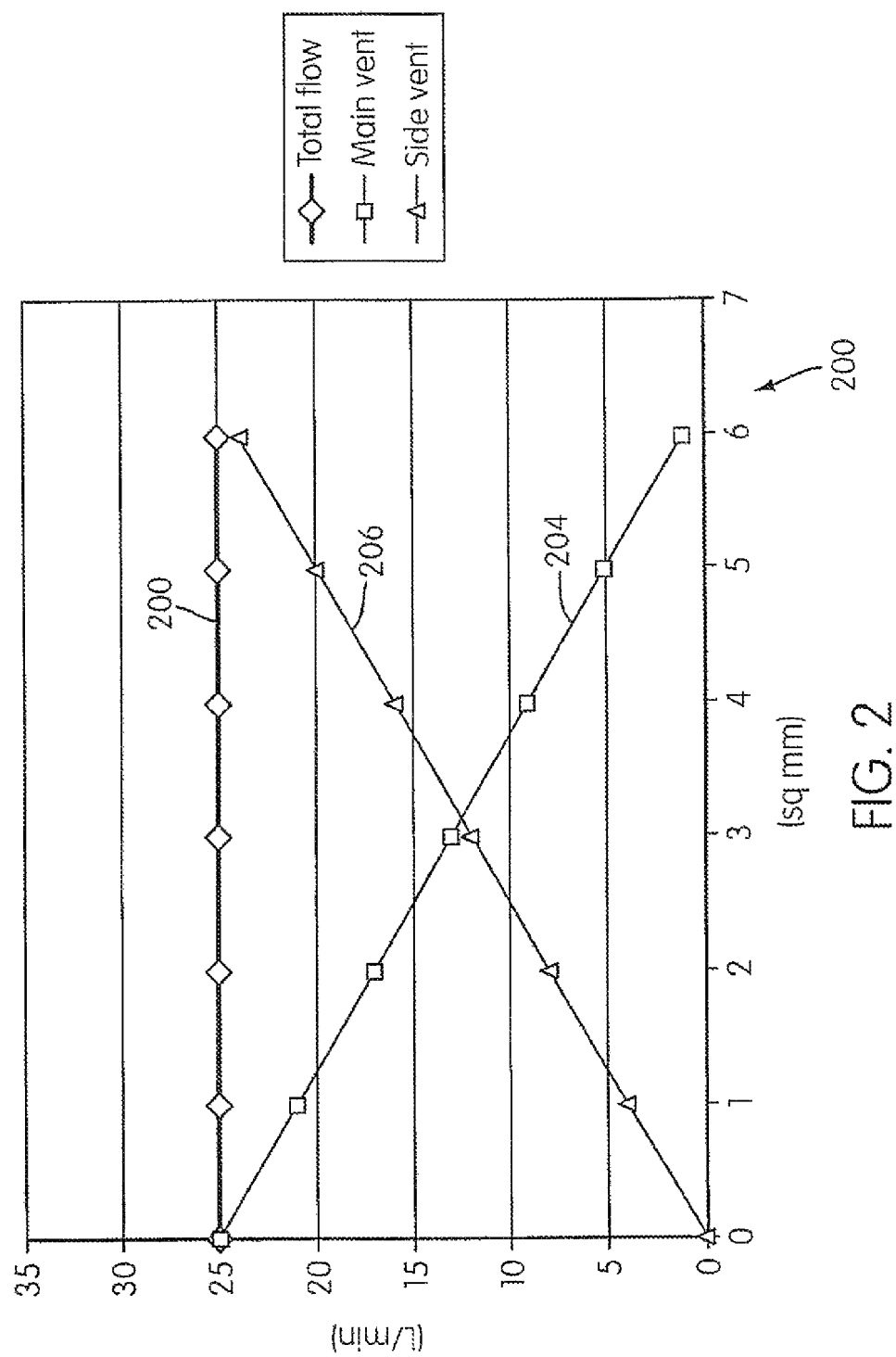
FIG. 2 illustrates the flow characteristics of a main vent and side vent in accordance with an embodiment of the present invention.

FIG. 2 is a graph that illustrates the flow characteristics of the main vent 106 and side vent 108 of the respiratory mask in accordance with an embodiment of the present invention. In FIG. 2, the flow rate is measured in units of liters per minute (L/min) along the y-axis. An index to indicate the build-up of debris on disk portion 102 is measured in units of millimeters squared along the x-axis. The total flow of air may be a constant value as indicated by line 200. The assembly may also operate at various pressures such that the line 200 would indicate variable flow rates at various flow pressures. When the disk portion is maintained in a clean condition, i.e., the debris build-up index is low, the flow rate through the main vent 106 is higher. The flow characteristics of the main vent 106 are shown as line 204. However, as the debris build-up index increases, the flow rate through the side vent 108 increases. The flow characteristics of the side vent 108 are shown as line 206.

The flow characteristics of the side vent 108 may be altered, for example, by changing the stiffness or biasing force of the bellows portion 104, by changing the diameter or area of the disk portion 102, by selecting material of various flow impedance characteristics for the disk portion 102, or by changing the opening size, number of and/or shape of the side vent 108.

The flow characteristics of the main vent 106 may be altered, for example, by changing the diameter or area of the disk portion 102, by selecting material of various flow impedance characteristics for the disk portion 102, by changing the opening size, number of and/or shape of the side vent 108, or by changing the stiffness or biasing force of the bellows portion 104.

Figure 3:
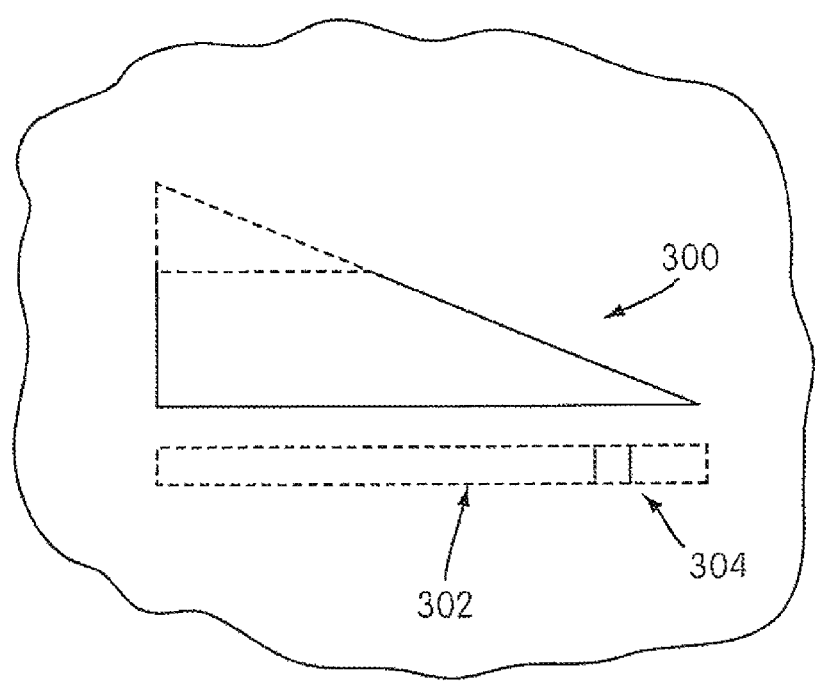
FIG. 3 illustrates a visual indicator of a disk condition in accordance with an embodiment of the present invention.

As an option to assist the user in ascertaining the amount of debris build-up on the disk portion 102, the vent assembly may include a mechanism to sense and/or indicate the condition of the disk portion 102. FIG. 3 illustrates a visual indicator 300 of a disk condition in accordance with an embodiment of the present invention. In FIG. 3, an indicator 304 that is attached to the disk portion 102 may be used to display, via a window 302, the level of debris build-up. Window 302 is preferably transparent.

The indicator 300 may perform sensing, for example, by an electro-mechanical contact or optical sensor. The sensing portion of the mechanism could preferably produce a pulse or continuous stream of energy that may be detected by a receiving device. Each of the received signals may be logged to create a database containing information that may be used to analyze various aspects of the vent assembly. For example, an event may be sensed by the mechanism and logged as an entry that the user may observe upon waking the next morning. In the alternative, an event may be sensed and an auditory or visual signal provided to the user immediately to indicate the occurrence of a particular condition or event in the vent assembly. The mechanism used to provide the auditory or visual signal may be, for example, attached to the disk portion 102 to indicate the amount of debris build-up and/or whether the disk portion 102 needs to be replaced.

The information about the vent condition provided by a sensing mechanism or other suitable device can have several uses. For example, a warning may be activated based on the information whereby a clogged condition can be logged. An auditory signal (arousing noise or synthetic voice warning) and/or visual signal can be given to the user. A visual signal can be discretely given via a readout on a display screen and noticed by the user when, for example, the user addresses the flow generator upon waking at the end of a normal sleep period. The visual signal can also be given by way of a light of sufficient brightness and/or intensity calculated to awaken the user.

The vent condition information can be converted into a signal which can be transmitted to a distant location. Preferably, the signal is transmitted via a public communication network such as the public telephone system or the Internet. Additionally, the vent condition information can be sent to a supplier or other appropriate receiver and used to automatically order a replacement vent, which can be dispatched automatically to the user.

The side vent 108 can be configured such that flow through the side vent 108 produces an audible sound, for example a whistling sound, to alert the user to debris build-up. Additionally, the vent assembly 100 can incorporate a microphone to monitor sounds produced by the vent assembly 100, in particular, sounds generated by air flow through the side vent 108. The sounds can be logged as an event, or they can be amplified to wake the user. The sounds can also be recorded or used to trigger an alarm or suitable device to alert the user to debris build-up, as explained above with respect to the vent condition information. Additionally, the vent assembly 100 can be configured such that movement of the disk portion 102 with respect to the vent assembly 100 causes an appropriate signal to be generated, such as a sound, visual indication or electronic signal.

In the event that there is stoppage of airflow to the respiratory mask, it is possible that a continuous positive flow of breathable air is not provided for the user to breathe. Flow stoppage can occur, for example, during a power failure in which the flow generator arranged to provide airflow does not operate. A vent assembly that allows flow out of the mask to the environment but does not allow flow into the mask from the environment could potentially cause the user to asphyxiate during flow stoppage. Accordingly, the vent assembly may be configured and arranged to include an anti-asphyxia feature, such as that illustrated in the vent assembly in FIGS. 4A and 4B. The anti-asphyxia feature can allow airflow into the mask from the environment during flow stoppage when the user inhales.

It is contemplated that an anti-asphyxia feature can be obtained by changing the orientation of the vent assembly 100 with respect to the mask frame 110. For example, the vent assembly 100 can be arranged such that the disk portion 102 faces outward away from the mask interior and the bellows portion 104 faces inward toward the mask interior. A vent assembly 100 with such an orientation can be provided in addition to an existing vent assembly 100 with a typical orientation to provide an anti-asphyxia feature to the typically oriented vent assembly 100.

Figure 4A:
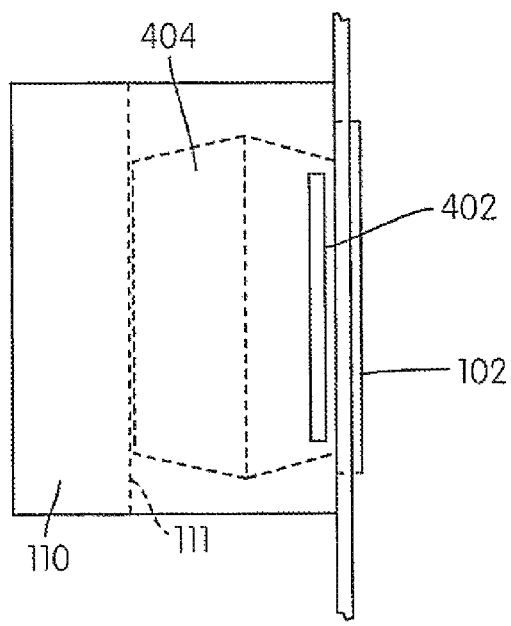
FIG. 4A illustrates an open, extra air path of an anti-asphyxia valve in accordance with an embodiment of the present invention.
Figure 4B:
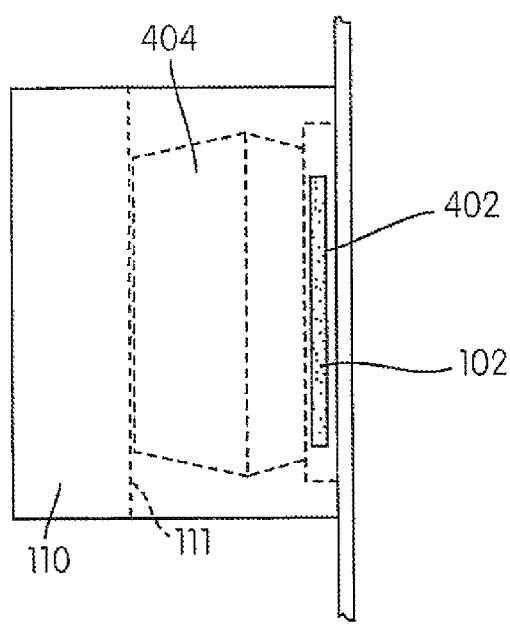
FIG. 4B illustrates a closed, extra air path of an anti-asphyxia valve in accordance with an embodiment of the present invention.

FIG. 4A shows an additional flow path 402 provided in the mask frame 110 to allow flow from the environment into the mask interior to prevent the user from asphyxiating during flow stoppage. The side vent 108 is not visible in this view, and the bellows portion 404 and the bellows stop 111 within the mask frame 110 are illustrated in phantom. When the user of the respiratory mask breathes in during flow stoppage, the bellows portion 404 stretches towards the mask interior (to the right as illustrated in FIG. 4A) and allows the disk portion 102 to move towards the mask interior. The movement of the disk portion 102 opens the flow path 402 and allows air to flow through flow path 402. Flow path 402 is configured such that slight displacement of disk portion 102 results in a relatively large opening in flow path 402. When a constant positive pressure exists in the mask interior, the bellows portion 404 is not stretched towards the mask interior, and the disk portion 102 can close the additional flow path 402. The closed flow path 402 is illustrated in FIG. 4B, and the disk portion 102 is visible through the flow path 402.

Figure 5A:
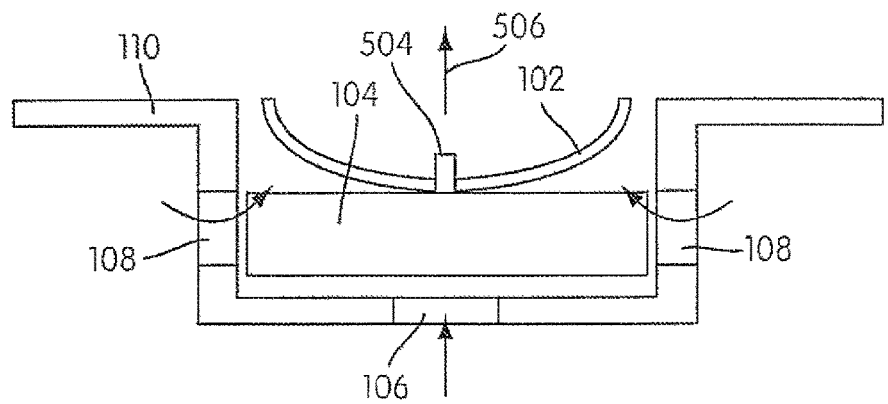
FIG. 5A illustrates an alternate anti-asphyxia valve during inhalation in accordance with an embodiment of the present invention.
Figure 5B:
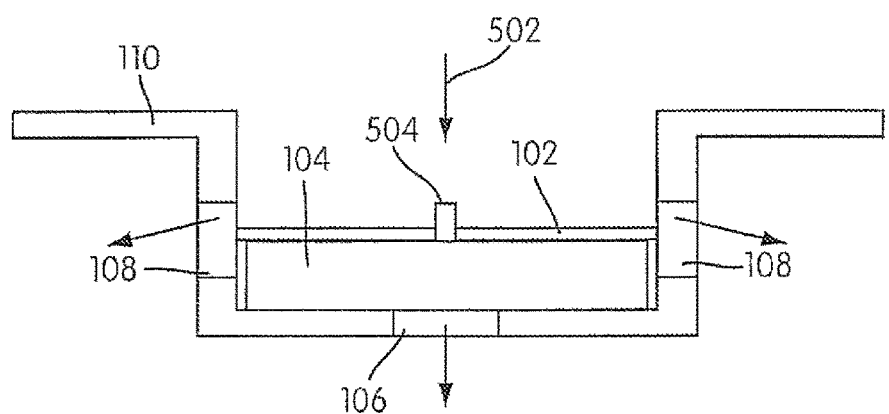
FIG. 5B illustrates an alternate anti-asphyxia valve with partial debris build up during exhalation in accordance with an embodiment of the present invention.
Figure 5C:
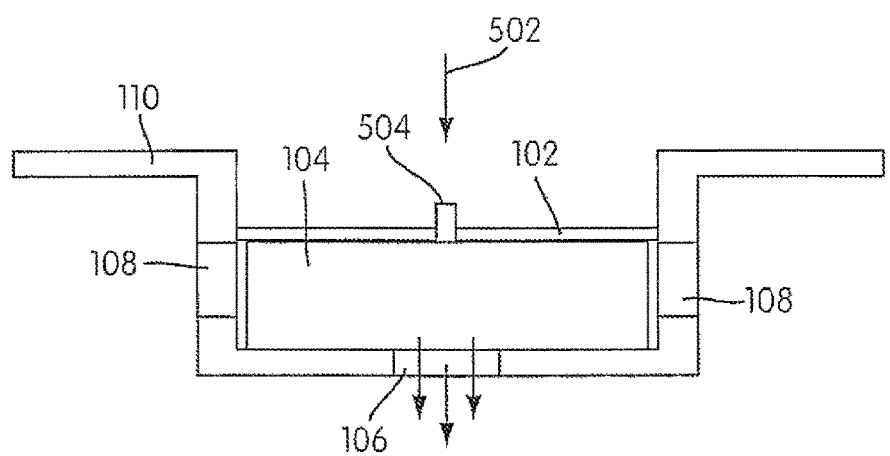
FIG. 5C illustrates an alternate anti-asphyxia valve with substantially no debris build up during exhalation in accordance with an embodiment of the present invention.

FIGS. 5A-5C illustrate an alternate anti-asphyxia valve that may be included in the vent assembly in accordance with an embodiment of the present invention. In FIGS. 5A-5C, disk portion 102 is made of a flexible material, for example, a membrane material, to permit the disk portion 102 to flex with respect to the bellows portion 104. Additionally, disk portion 102 may be connected to the vent assembly at the center of bellows portion 104 by a fastener 504 to permit maximum flexibility of the disk portion 102. FIGS. 5A-5C also show two side vents 108.

FIG. 5A illustrates the anti-asphyxia valve during flow stoppage when the user of the respiratory mask frame 110 inhales. Flow in the direction of arrow 506 flexes disk portion 102 towards the inside of the mask frame 110. Air entering the mask frame 110 via main vent 106 and side vents 108 results in airflow in the direction of arrow 506, even when the disk portion 102 may have substantial debris blockage.

FIG. 5B illustrates the anti-asphyxia valve when the disk portion 102 has partial debris blockage during use. Airflow in the direction of arrow 502 caused by constant positive pressure in the respiratory mask frame 110 and/or exhalation by the user can push disk portion 102 against bellows portion 104, compressing the bellows portion 104 (i.e., the primary flow path via the disk portion 102 is partially blocked resulting in secondary air flow via the side vents 108) such that air flows from the mask frame 110 via the main vent 106 and side vents 108. Airflow via the main vent 106 and the side vents 108 depends at least upon the amount of debris blockage of the disk portion 102. As illustrated, the bellows portion 104 is partially compressed, indicating partial debris blockage of the disk portion 102.

FIG. 5C illustrates the anti-asphyxia valve when the disk portion 102 is substantially clean and free of debris blockage during use. Airflow in the direction of arrow 502 slightly pushes disk portion 102 against bellows portion 104. However, because the disk portion 102 is substantially clean, the bellows portion 104 is not substantially compressed by the primary air flow. Accordingly, air flows from the mask frame 110 via the primary flow path through the main vent 106. Air flow via the secondary flow path through side vents 108 is substantially minimized.

Figure 6A:
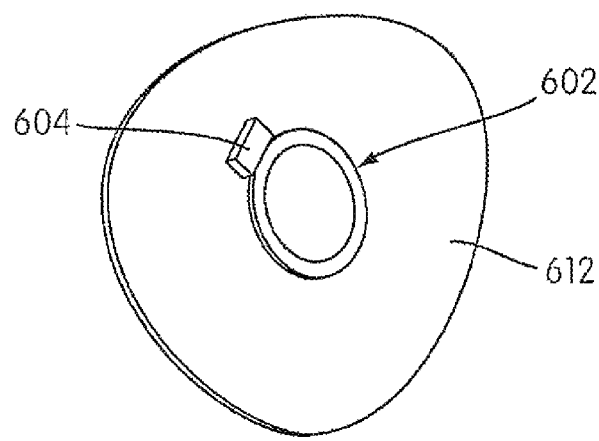
FIG. 6A illustrates a respiratory mask having a vent assembly in accordance with another embodiment of the present invention.

FIG. 6A illustrates a vent assembly of a respiratory mask in accordance with another embodiment of the present invention. The mask housing 612 includes an orifice 610 (see FIG. 6B) and a flap portion 602 that is held in position over the orifice 610 by a retainer mechanism 604. Typically, the flap portion 602 and the retainer mechanism 604 of the vent assembly are located on the exterior of the mask housing 612 such that they do not interfere with the operation of other aspects of the mask, such as the coupling of the mask to a flow generator or operation of any mask ports or any user interfaces such as facial cushions.

The orifice 610 and vent assembly are also located such that the operation of the vent assembly is not readily subject to interference by the user or the user's environment, especially during sleep. An exemplary location of the orifice 610 and vent assembly in the mask housing 612 is at a position to the right or left of the user's nose on a side of the mask. Alternatively, multiple vents can be provided. Two vents can be used, one located on each side of the mask to the right and to the left of the user's nose.

Figure 6B:
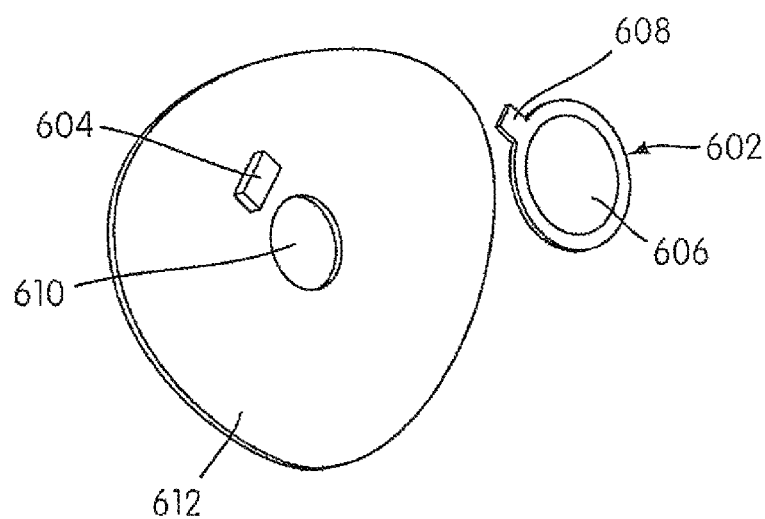
FIG. 6B illustrates an exploded view of the vent assembly of FIG. 6A.

FIG. 6B illustrates an exploded view of the vent assembly of FIG. 6A. Flap portion 602 may be made of a flexible material, and an interior section may be covered with a porous mesh material 606. The mesh material 606 of the flap portion 602 is configured to cover the orifice 610 having a predetermined diameter. The flap portion 602 is held in position over the orifice 610 via an insert portion 608 configured to fit retainer mechanism 604.

In FIG. 6B, orifice 610 functions as a main vent portion to regulate the airflow of the respiratory mask such that the direction of primary airflow is through the mesh material 606 of the disk portion 602. However, as debris build-up accumulates on mesh material 606, a gap can develop between the mask housing 612 and the flap portion 602. The size of the gap, created by movement of the flap portion 602 away from mask housing 612, can be proportional to the force applied by flow pressure to the flap portion 602. The force can be proportional to the increased total projected area caused by debris build-up on the mesh material 606. The gap between the mask housing 612 and the flap portion 602 can provide a secondary airflow path bypassing the flap portion 602.

The return force or biasing force of flap portion 602 to return to its position on mask housing 612 can depend upon the flexibility of the material of the flap portion 602 and the shape and/or thickness of the insert portion 608. For example, flap portion 602 may be made from a silicone material, and mask housing 612 may be made from a polycarbonate or other similar material. The selection of silicone for the flap portion 602 and polycarbonate for the mask housing 612 would create a high static attraction between the flap portion 602 and the mask housing 612. The high static attraction between the flap portion 602 and the mask housing 612 may be used to augment or serve as the return force or biasing force of the flap portion 602. Retainer mechanism 604 can incorporate a hinge mechanism and/or a spring to vary the return force of the flap portion 602.

The flap portion 602 can be made as a disposable item. The relatively simple construction can allow for a low cost of manufacture. Accordingly, the flap portion 602 can be disposed of and replaced as an alternative to being cleaned. Additionally, the flap portion 602 can be installed easily into the retainer mechanism 604, without complicated disassembly of the vent assembly or mask. The user can readily remove and dispose of a clogged flap portion 602 and install a clean flap portion 602.

The following exemplary dimensions in Table 1 can be used to provide a flow rate of 20 L/min during a positive internal mask pressure of 2 cm H$_2$O when using the embodiment illustrated in FIGS. 6A and 6B:

TABLE 1

| | |
|---|---|
| Orifice Diameter | 3 mm |
| Mesh Material Diameter | 10 mm |
| Mesh Material | Nylon |
| Flap Portion Diameter | 20 mm |
| Insert Portion Width | 9 mm |
| Insert Portion Thickness | 0.12 mm |
| Flap/Insert Portion Material | Polyester |

It is contemplated that the above dimensions can be reduced if multiple vent assemblies are provided. For example, if two vent assemblies are provided, the above dimensions can be halved for each vent assembly to effectively achieve the same flow rate.

The embodiment of a vent assembly illustrated in FIGS. 6A and 6B can incorporate an anti-asphyxia feature in the form of an auxiliary orifice (not shown) with a corresponding auxiliary flap and retainer mechanism (not shown) configured to allow airflow from the environment into the mask during flow stoppage when the user inhales. For example, the auxiliary flap can be arranged on the inside of the mask surface to seal the auxiliary orifice such that inhalation in the absence of normal airflow causes the flap to deflect inwards and allow air from the environment through the auxiliary orifice into the mask for the user to breathe. The auxiliary flap can be non-porous to prevent flow therethrough and to prevent debris buildup on the auxiliary flap. The auxiliary flap can be configured and arranged such that pressure required to cause inward deflection of the auxiliary flap is low. Accordingly, the user does not experience difficulty in breathing during flow stoppage. It is contemplated that the auxiliary orifice and flap can provide an anti-asphyxia feature to a mask incorporating other embodiments of a vent assembly (for example, the vent assembly 100 illustrated in FIGS. 1A and 1B).

An anti-asphyxia feature can be incorporated into the flap portion 602, insert portion 608, retainer mechanism 604 and orifice 610 by using a flap portion 602 with an outer diameter equal to the inner diameter of the orifice 610 so that a pressure seal can develop between the flap portion 602 and the orifice 610, while allowing the flap portion 602 to deflect inwards during flow stoppage when the user inhales. Preferably, the insert portion 608 and/or the retainer mechanism 604 are constructed such that deflection away from the mask interior maintains a predetermined flow characteristic, while deflection towards the mask interior allows the user to breathe easily. For example, the insert portion 608 can be biased such that inward deflection occurs more easily than outward deflection. Additionally, a hinge can be incorporated to allow inward deflection under a low force, while outward deflection requires a higher force commensurate with desired flow characteristics. Alternatively, the flap portion 602 and the retainer mechanism 604 can be arranged on the inside of the mask such that outward deflection of the flap portion 602 away from the mask interior through the orifice 610 requires a higher force than inward deflection. Accordingly, the user can breathe easily during flow stoppage.

Figure 7A:
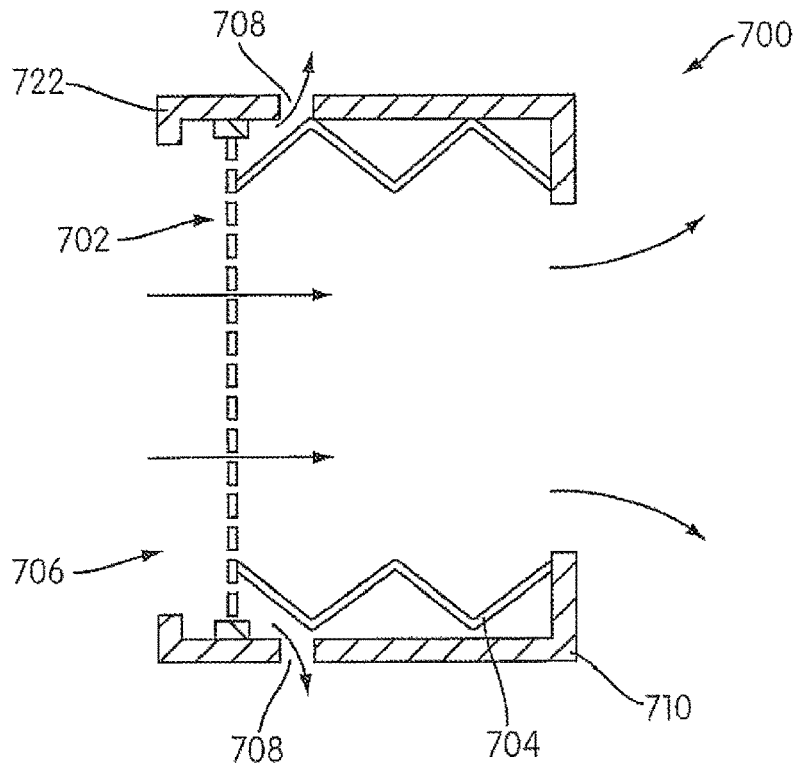
FIG. 7A illustrates a vent assembly in accordance with another embodiment of the present invention.

FIG. 7A is a cross-sectional view of a vent assembly 700 of a respiratory mask in accordance with another embodiment of the present invention. The vent assembly 700 includes a disk portion 702, a bellows or spring biasing portion 704 and a main vent 706 arranged in a mask housing or valve housing 710. A plurality of side vents 708 are formed in the valve housing 710. Preferably the valve housing 710 is cylindrical. The valve housing 710 can further be arranged to provide a disk stop 722 to retain the disk portion 702 within the valve housing 710 against a force created by the spring portion 704 applied to the disk portion 702.

Figure 7B:
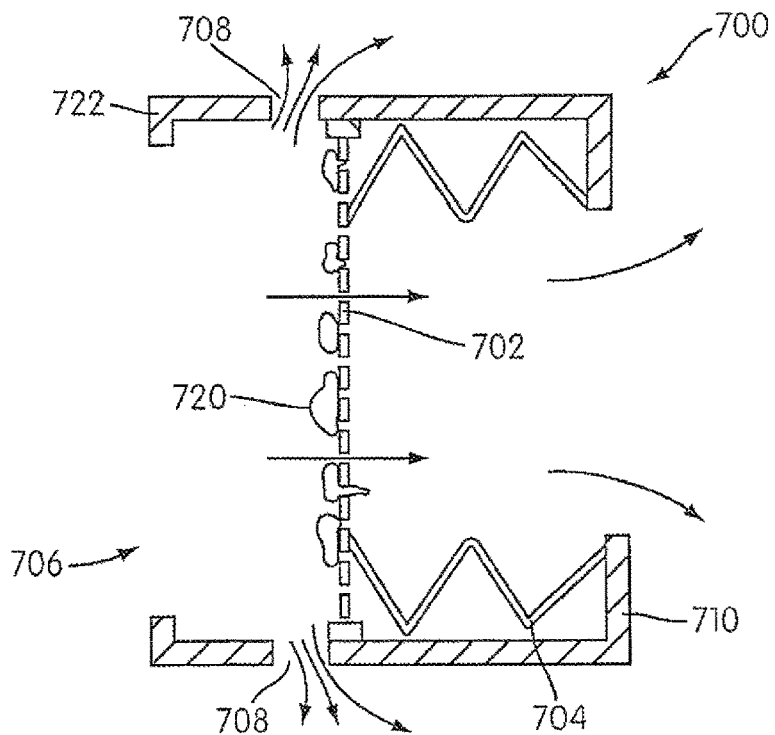
FIG. 7B illustrates the vent assembly of FIG. 7A with debris blockage.

A spring force from the biasing portion 704 can maintain the disk portion 702 in a sealed position against the main vent 706 portion such that the side vents 708 are not substantially exposed to a primary flow path such that a majority of flow passes through the disk portion 702. The biasing force exerted by the biasing portion 704 upon the disk portion 702 is greater than or equal to the force exerted by flow pressure upon a projected area of the disk portion 702 when the disk portion 702 is in a clean condition. As shown in FIG. 7B, debris 720 can accumulate on the disk portion 702. As debris 720 accumulates, the force exerted by flow pressure increases, causing the biasing portion 704 to compress in the direction of flow and causing the disk portion 702 to move with respect to the valve housing 710 away from disk stop 722.

When the biasing portion 704 is compressed by the force exerted by flow pressure, the disk portion 702 can be positioned to allow flow through a plurality of side vents 708. Side vents 708 can have a wedge shape (as shown in FIGS. 1A and 1B) or other suitable shape, depending upon desired secondary flow characteristics of the vent assembly 700. Alternatively, additional vents can be arranged further along the path of movement of the disk portion 702 beyond side vents 708 such that they are exposed to airflow at various levels of displacement as the disk portion 702 is displaced by flow pressure. Biasing portion 704 can be a spring. Because it is not necessary to provide a flow path through the biasing portion 704, the biasing portion 704 can be a bellows constructed using a suitable material such as silicone, which prevents airflow therethrough. It is contemplated that the bellows can be constructed from a porous material or can be permeated with holes to allow airflow, and can incorporate a predetermined airflow impedance.

Figure 8A:
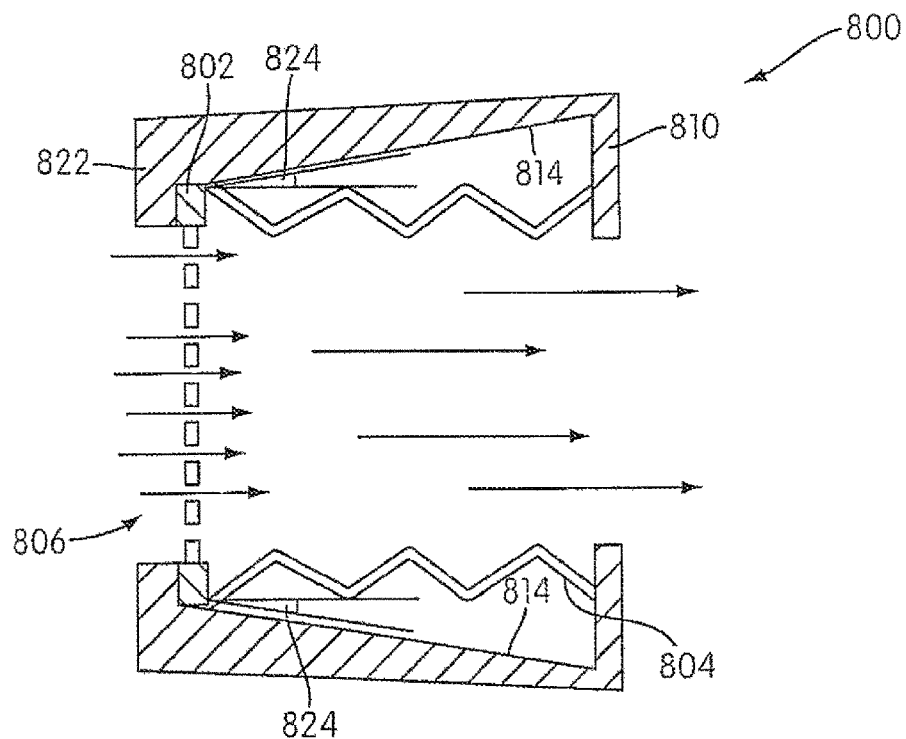
FIG. 8A illustrates a vent assembly in accordance with yet another embodiment of the present invention.

FIG. 8A is a cross-sectional view of a vent assembly 800 of a respiratory mask in accordance with yet another embodiment of the present invention. The vent assembly 800 includes a disk portion 802, a spring or bellows biasing portion 804, and a main vent 806 arranged in a valve housing 810. Unlike the embodiment shown in FIGS. 7A and 7B, the vent assembly 800 does not include side vents, although side vents can be used to augment the embodiment shown in FIG. 8A. The valve housing is preferably cylindrical and is arranged to provide a disk stop 822 to retain the disk portion 802 within the valve housing 810.

The disk portion 802 can move with respect to the valve housing 810, against the biasing pressure of the biasing portion 804, along the direction of flow through the main vent 806. The valve housing 810 is further arranged such that at least a portion of the inner walls 814 of the valve housing 810 form a draft angle 824 between the direction of movement of the disk portion 802 and the inner walls 814 of the valve housing 810.

Figure 8B:
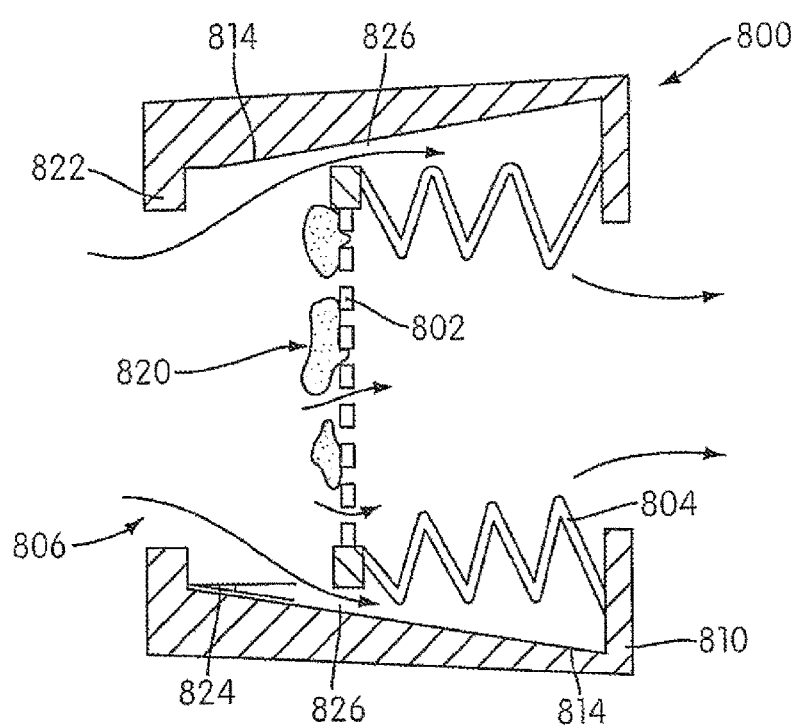
FIG. 8B illustrates the vent assembly of FIG. 8A with debris blockage.

As illustrated in FIG. 8B, build-up of debris 820 causes pressure from primary flow to displace the disk portion 802 in the direction of flow. Due to the draft angle 824 of at least a portion of the inner walls 814, a gap 826 is developed between the inner walls 814 and a peripheral of the disk portion 802. Accordingly, secondary airflow can bypass the disk portion 802 via the gap 826. Because the secondary flow takes a secondary pathway including the biasing portion 804, the biasing portion 804 preferably can transmit the secondary flow. The biasing portion 804 can be a spring. In embodiments where biasing portion 804 is a bellows, the bellows is constructed with suitable porous or permeated material to accommodate the secondary flow. The flow impedance of the biasing portion 804 also can be used to vary the secondary flow characteristics of the vent assembly 800.

The draft angle 824 illustrated in FIGS. 8A and 8B is approximately 5-15 degrees, and preferably 10 degrees. The angle preferably remains substantially constant along the extent of the entire inner wall 814. Accordingly, the gap 826 increases proportionately in relation to the displacement of the disk 802. However, it is contemplated that the draft angle 824 can be greater than or less than 5-15 degrees, and the draft angle 824 can vary along the extent of the inner wall 814 (i.e., the inner wall 814 can be curved), depending upon the desired secondary flow characteristics and desired development of the gap 826 throughout the displacement of the disk portion 802.

Additionally, only a circumferential portion of the inner wall 814 along the circumference of the valve housing 810 can be shaped to include the draft angle 824, whereas the remaining portions of the inner wall 814 along the circumference of the valve housing 810 can remain perpendicular to the displacement of the disk portion 802. Portions of the inner wall 814 perpendicular to the displacement of the disk portion 802 can act as a guide to stabilize the disk portion 802 during displacement.

Figure 9A:
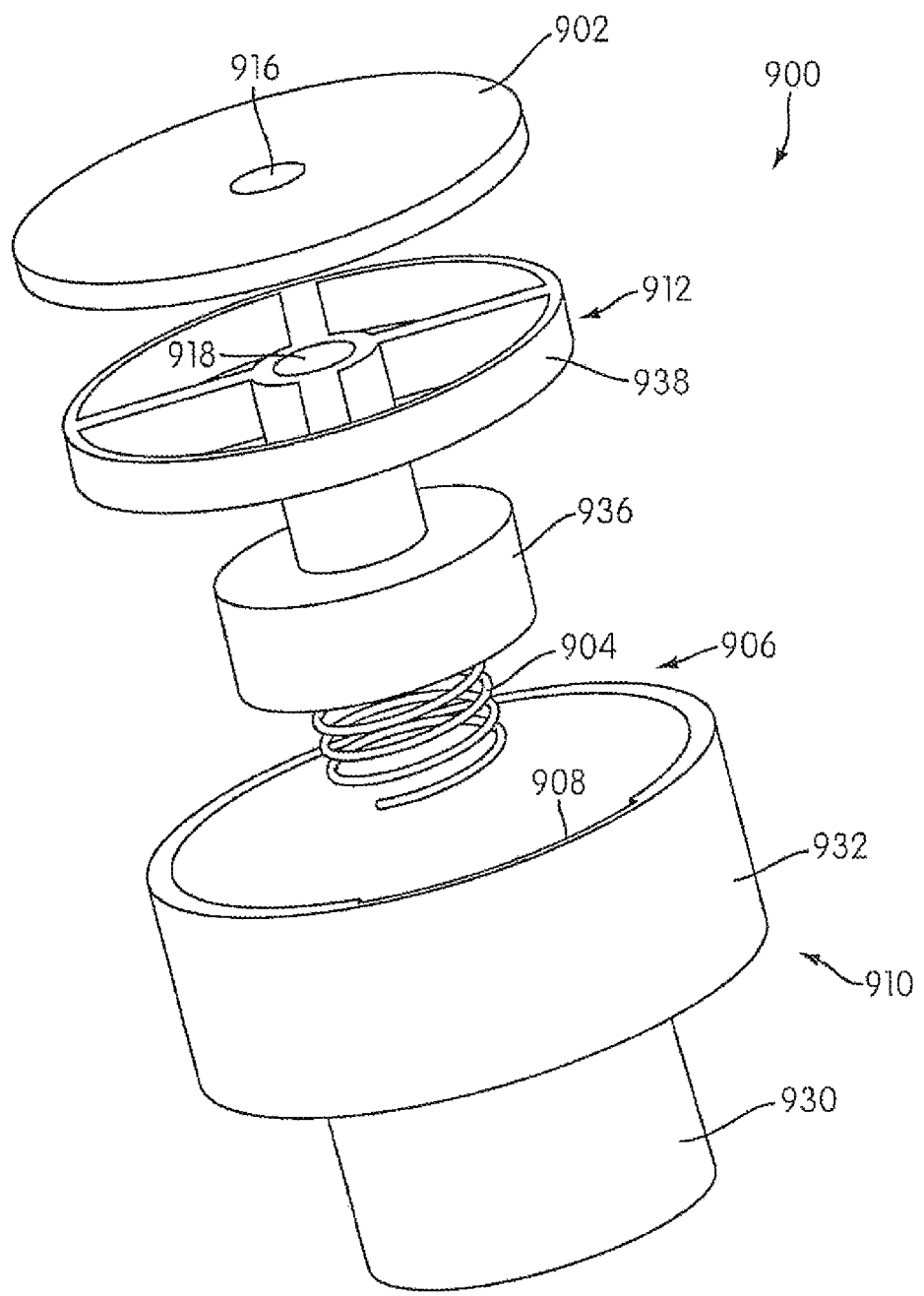
FIG. 9A illustrates a vent assembly in accordance with yet another embodiment of the present invention.

FIG. 9A illustrates a vent assembly 900 of a respiratory mask in accordance with yet another embodiment of the present invention. The vent assembly 900 includes a valve housing 910, a spring biasing portion 904, a holder portion 912, and a disk portion 902. The valve housing 910 is composed of a first portion 930 and a second portion 932. The first portion 930 and the second portion 932 are illustrated as hollow cylinders arranged and connected to each other coaxially, the second portion 932 having a diameter greater than the diameter of the first portion 930. The first portion 930 forms a recess 934 (see FIG. 9B). The second portion 932 forms a main vent 906 shaped to allow airflow to pass within the inner circumference of second portion 932, through a plurality of passages 928 at the interface between the first portion 930 and the second portion 932 (see FIG. 9B), and along the outer circumference of the first portion 930. The diameters of the first portion 930 and the second portion 932 are chosen to correspond to diameters of respective parts (base portion 936 and receiving portion 938) of the holder portion 912.

The holder portion 912 includes a base portion 936 and a receiving portion 938. The base portion 936 of the holder portion 912 slidably engages the recess 934 of the first portion 930. The receiving portion 938 of the holder portion 912 is sized to slidably engage at least a portion of the inner circumference of the main vent 906 of the valve housing 910.

The biasing portion 904 engages the base portion 936 of the holder portion 912 and engages the first portion 930 of the valve housing 910. The biasing portion 904 provides a spring force between the valve housing 910 and the holder portion 912, allowing the holder portion 912 to slide along the axis of the valve housing 910. The holder portion 912 accordingly can move with respect to the valve housing 910.

The porous disk portion 902 is attached to the receiving portion 938 of the holder portion 912. The disk portion 902 sealably engages at least a portion of the inner circumference of the second portion 932 of the valve housing 910. Preferably, a majority of the outer circumference of the disk portion 902 sealably engages at least a portion of the inner circumference of the main vent 906.

The disk portion 902 can be fixedly secured to the receiving portion 938 of the holder portion 912 using glue or other suitable adhesive. The disk portion 902 also can be mounted to the receiving portion 938 via a central fastener (not shown) passing through a disk hole 916 in the disk portion 902 and anchored to a holder hole 918 in the holder portion 912. The disk portion 902 and the holder portion 912 are shaped to receive the central fastener. The central fastener can mount the disk portion 902 to the receiving portion 938 without the use of glue, allowing all or portions of the disk portion 902 to separate from the receiving portion 938 under specific flow conditions.

Separation of all or portions of the disk portion 902 from the receiving portion 938 can provide an anti-asphyxia feature similar to the anti-asphyxia feature of the embodiment illustrated in FIGS. 5A-5C. To provide the anti-asphyxia feature in the vent assembly 900, the porous disk portion 902 is preferably made of a flexible material which can flex away from the receiving portion 938 to break a seal with the inner circumference of the main vent 906, depending upon flow conditions and debris build up in use. Alternatively or additionally, the anti-asphyxia feature can be accomplished by using a flexible central fastener (not shown) for the disk portion 902. A flexible central fastener can flexibly extend and allow the disk portion 902 to separate from the receiving portion 938 and the inner circumference of the main vent 906, even if the disk portion 902 is not flexible. A spring also can be used in conjunction with the central fastener to allow displacement of the disk portion 902, depending upon flow conditions and debris build up in use.

Figure 9B:
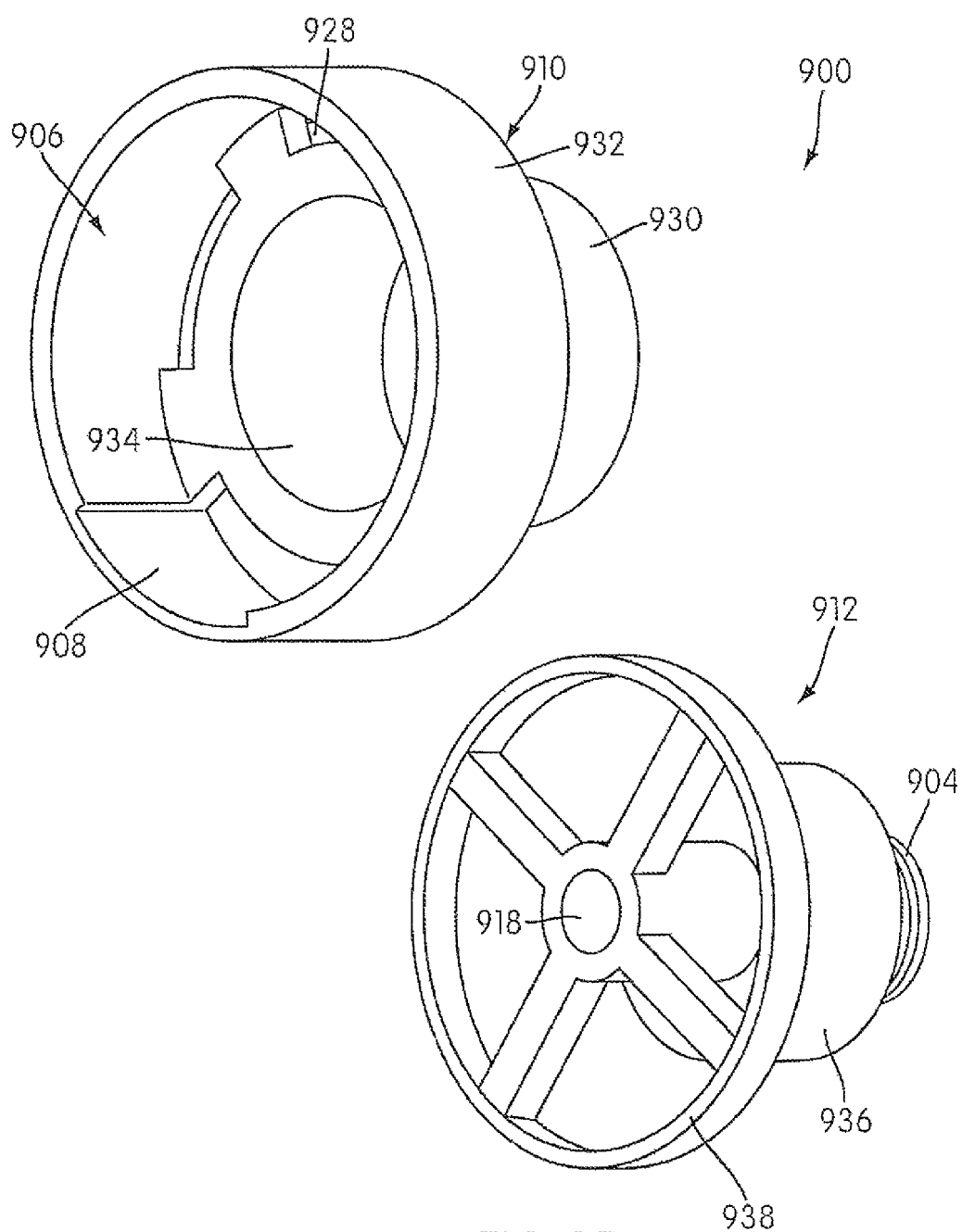
FIG. 9B illustrates a valve housing, a holder portion and a spring portion of the vent assembly of FIG. 9A.

FIG. 9B illustrates the valve housing 910 in more detail. The second portion 932 of the valve housing 910 includes at least one side vent 908. As illustrated, the side vent 908 is in the form of a groove having a tapering depth along an axial extent of the second portion 932. In particular, the depth of the side vent 908, i.e., the radial distance from the axis of the second portion 932 to the side vent 908, increases as the side vent 908 extends axially towards the first portion 930 of the valve housing 910. The side vent 908 is illustrated as occupying the entire axial extent of the second portion 932. Accordingly, the disk portion 902 does not sealably engage the side vent 908 of the second portion 932, but rather, the disk portion 902 sealably engages the remaining circumference of the second portion 932 not occupied by the side vent 908.

FIG. 9B illustrates a plurality of passages 928 formed in the valve housing 910 at the interface between the first portion 930 and the second portion 932. In use, air can flow through a primary flow path including the porous disk portion 902 and the plurality of passages 928 in the valve housing 910. When the disk portion 902 is substantially free of debris blockage, the biasing portion 904 can maintain the disk portion 902 in an upper position. In the upper position, a cross sectional area of the side vent 908 is minimized. Accordingly, secondary flow through the side vent 908 is minimized.

As the disk portion 902 becomes blocked with debris, the flow pressure causes the disk portion 902 to move towards a lower position. As the disk portion 902 moves towards the lower position, the cross sectional area of the side vent 908 increases. The increase in the cross sectional area of the side vent 908 allows an increase in secondary flow through the side vent 908, compensating for the decrease in primary flow through the disk portion 902 caused by debris blockage.

It is contemplated that, in alternate embodiments, the side vent 908 does not occupy the entire axial extent of the second portion 932. For example, the side vent 908 can occupy a lower portion of the second portion 932, i.e., a part of the second portion 932 nearer to the first portion 930. Accordingly, the disk portion 902 would sealably engage the entire circumference of the second portion 932 when the holder portion 912 is in the upper position. It is also contemplated that a plurality of side vents 908 can be used. Additionally, the side vent 908 can be arranged such that the circumferential width of the groove formed by the side vent 908 varies. The circumferential width of the side vent 908 can vary in addition to or as an alternative to varying the radial depth, to provide a varying cross sectional area of the side vent 908 throughout the range of movement of the holder portion 912 between the upper and lower positions.

Varying the circumferential width of the side vent 908 can allow for a consistently minimized radial depth of the side vent 908 while still providing a varying cross sectional flow area of the side vent 908 throughout the range of movement of the holder portion 912. For example, the side vent 908 can have a wedge shape similar to the shape of the side vent 108 illustrated in FIGS. 1A and 1B. A minimized radial depth of the side vent 908 can allow for a minimized radial thickness of the second portion 932 of the valve housing 910, compared to an increased thickness of the second portion 932 to accommodate the varying radial depth of the side vent 908. A reduction in the radial thickness of the second portion 932 of the valve housing 910 can minimize the overall size of the valve housing 910.

While not illustrated in detail in FIGS. 4A-9B, it is contemplated that the illustrated embodiments of a vent assembly can incorporate a visual indicator and/or sensing mechanism. An anti-asphyxia valve can be incorporated, in the form of an additional flow path provided in the mask and/or valve housing, and/or in the form of a flexible material in the disk portion. Additionally the valve assembly can be formed in a non-cylindrical shape.

FIGS. 10-24 illustrate an oxygen diverter valve which can be used independently of, instead of, or in conjunction with the valve described above. The oxygen diverter valve can be used for any air or oxygen delivery system in which there is some type of flow generator connected to a tube or airflow conduit with oxygen injection which is thereafter secured to a face mask. The transmitted gas can be any type of breathable or therapeutic gas.

Figure 10:
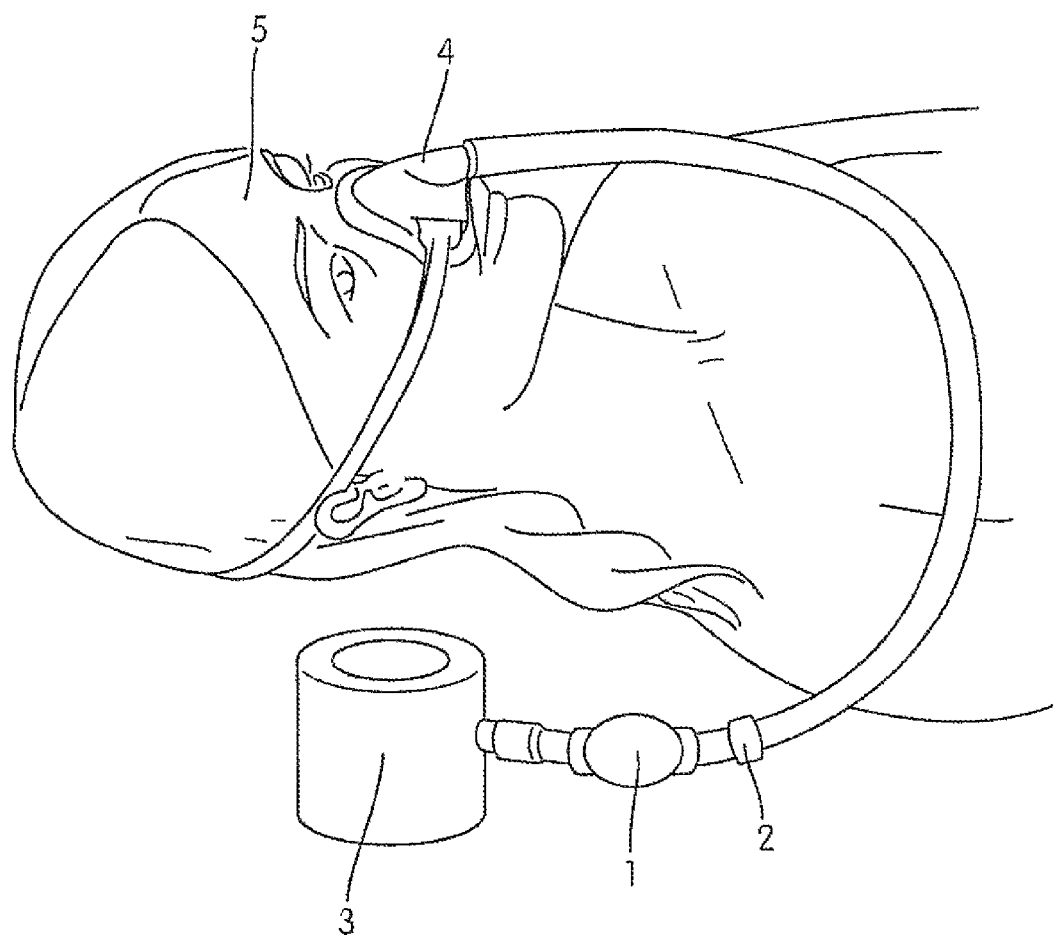
FIG. 10 is a general schematic drawing of a system comprising a flow generator being connected to a valve and mask via tubing in which the mask is connected to a patient, according to another embodiment of the present invention.

The general schematic of this is shown in FIG. 10 where flow generator 3 with a flexible airflow conduit which is secured to an embodiment of a valve 1 of the present invention. The oxygen injection point 2 is located downstream of the valve 1 and is thereafter connected to a nasal mask 4 of a patient 5. The mask shown is just one example of numerous types of patient interface.

The location of the valve 1 shown in FIG. 10 is just one example of numerous possible locations. The valve 1 should preferably be placed between flow generator 3 (or the equipment that is to be shielded from the oxygen) and the oxygen injection point 2.

The flow generator 3 produces a flow of breathable gas, typically air, and can be an electric blower, a controlled bottled gas system, a ventilator, or any other type of device that delivers breathable, therapeutic or anaesthetic gas.

Figure 11:
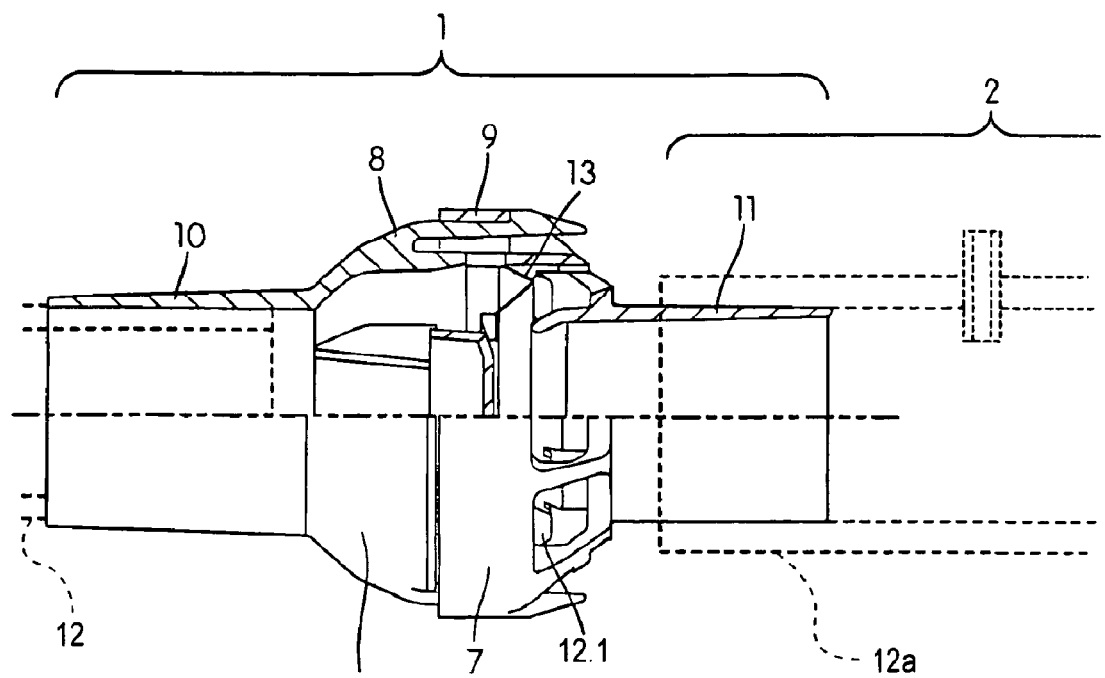
FIG. 11 is a side view/cutaway view of a valve of the present invention.

The valve 1 shown in FIG. 11 is comprised of two housing parts 6 and 7 which may be locked together by way of respective male and female clip fittings 8 and 9. The housing part 6 includes an inlet in the form of a female conical portion 10. The housing part 7 includes an outlet in the form of male conical portion 11. The portions 10 and 11 allow push-on assembly and frictional engagement with the gas supply conduit 12 and the oxygen supply conduit 12a, respectively. The housing part 7 includes one or more peripherally arranged vents 12a.

In the embodiment shown in FIGS. 11 to 14, a preferably flexible flap 13 of generally round cross-section is formed from a silicone rubber and has a central orifice.

Figure 12:
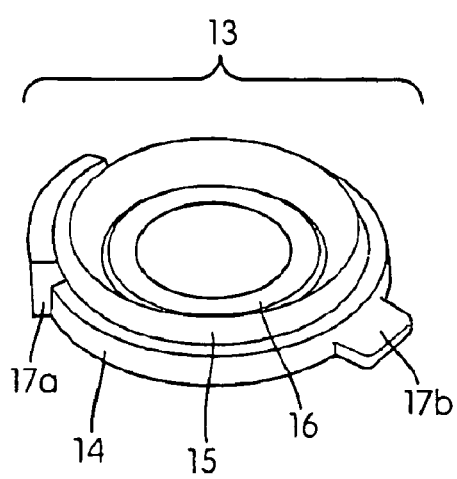
FIG. 12 is a perspective view of an embodiment of a flap according to the present invention.

As shown in FIG. 12 the flap 13 includes a first portion in the form of outer rim 14. The outer rim 14 is clamped or otherwise attached or mounted into a corresponding recess in the housing part 7. Cast-on lugs 17a and 17b are used when positioning the flap 13.

Figure 13:
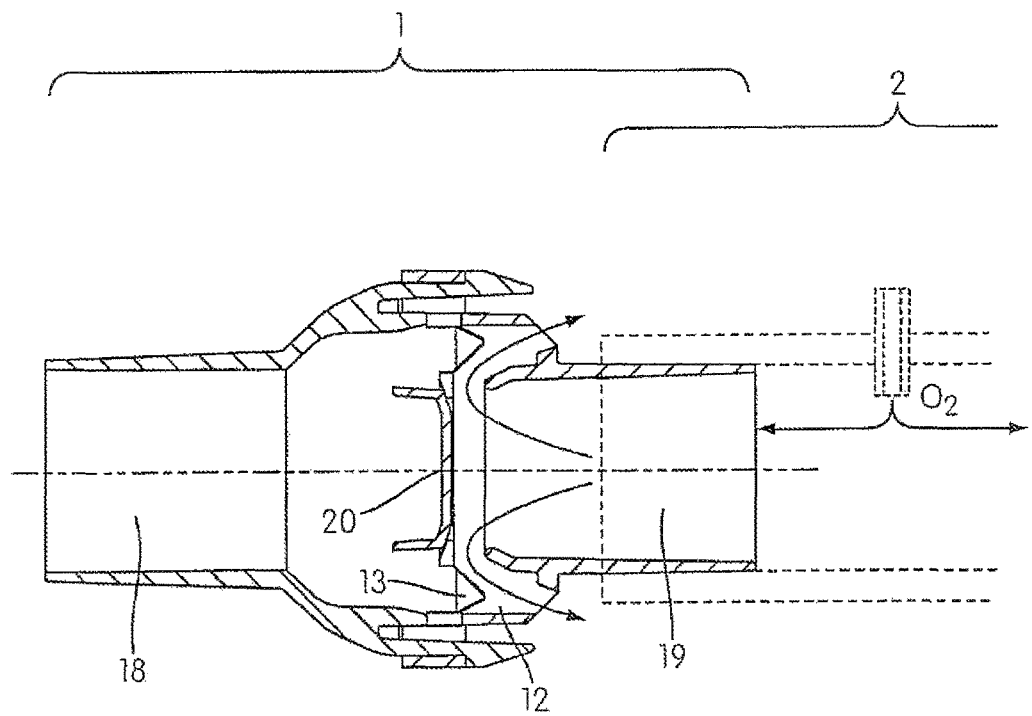
FIG. 13 is a cross sectional view of FIG. 11 in which the flow generator is not operating.
Figure 14:
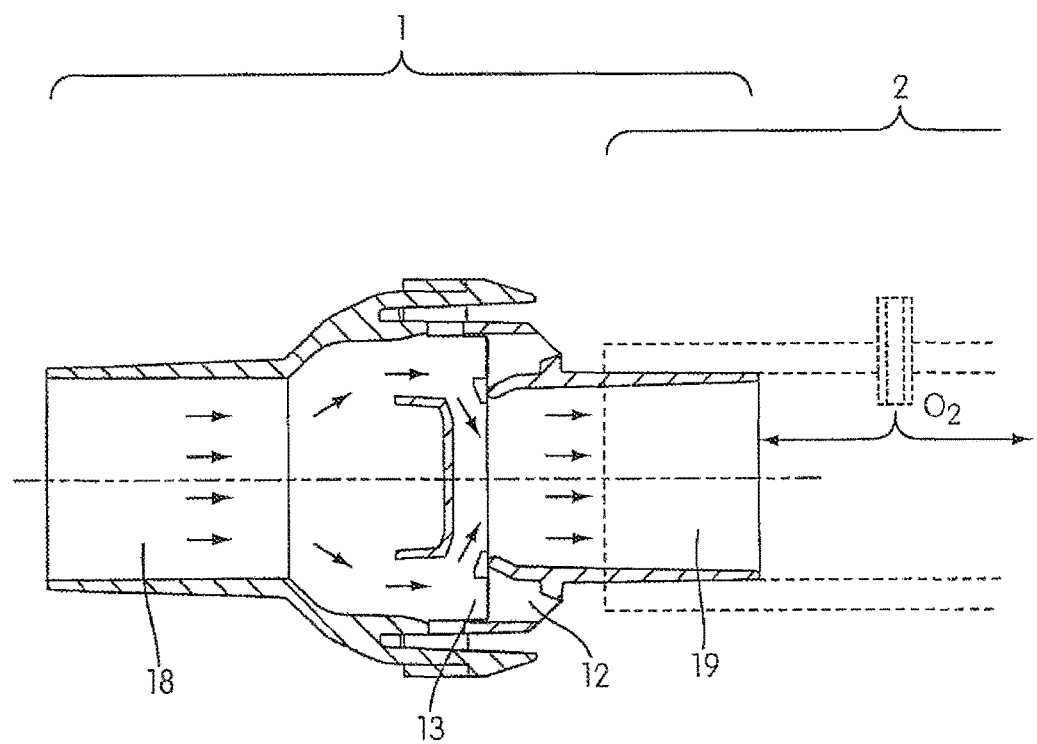
FIG. 14 is a cross sectional view of the valve of FIG. 11 in which the flow generator is operating and generating a pressure differential above the operating threshold.

The flap 13 includes a second portion in the form of a flexible hinged silicone membrane 15. The hinge shape allows the flap 13 to flex between the closed and open positions, as shown in FIG. 13 and FIG. 14 respectively. A third portion 16 resists crinkling or bending of the membrane. Third portion 16 includes a stiff toroid part which forms the actual seal.

The flap 13 is preferably manufactured by moulding of a single silicone rubber component in the shape shown in FIG. 12 (closed position). In the preferred embodiment the flap 13 is nominally 0.15 mm thick. The thickness of the flap is adjusted to suit its application and, in particular, the operating threshold pressure. If the flap is too flimsy it may not close at the correct pressure and if it is too stiff the flap will not open at the correct pressure.

As shown in FIG. 13, when the difference in the gas pressure between air inlet cavity 18 and the atmosphere is below a predetermined operating threshold of, for example 2 cm $H_2O$, the flap 13 is in a relaxed (closed) state. The toroid 16 is resting on the valve core 20 blocking the oxygen rich gas flow from the oxygen injection cavity 19 from entering the air inlet cavity 18. The gas flows from the oxygen injection cavity 19 through the vents 12 to the atmosphere.

When the gas supply from the flow generator 3 commences or resumes and the difference in the gas pressure between the air inlet cavity 18 and the atmosphere builds up to equal or above 2 cm $H_2O$, the flap 13 moves to an "open" position whereby vents 12 are closed as shown in FIG. 14. The flap 13 is kept open as long as the pressure in the air inlet cavity 18 remains above the predetermined operating threshold. In the open position all the gas supplied from the flow generator 3 passes through the orifice of the flap 13 into the air injection cavity 19, mixes with the oxygen supplied and is delivered to the patient via the facemask.

The inherent resilience of the flap 13 re-closes the valve and re-opens vents 12 when the pressure difference between the air inlet cavity 18 and atmosphere falls below the predetermined operating threshold.

Testing of a prototype of the valve 1 shown in FIGS. 10 to 14 was conducted with a flow generator connected to the inlet cylindrical portion 10 via an airflow conduit. An oxygen supply and a mask were connected to the valve 1 at the outlet cylindrical portion 11 simulating normal use. With this arrangement the valve had an operating threshold of less than 2 cm $H_2O$ pressure difference.

Figure 15:
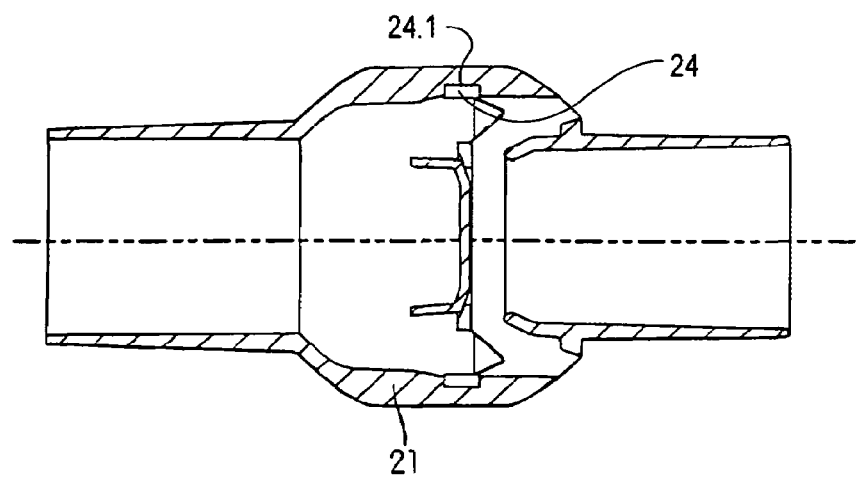
FIG. 15 is a cross sectional view of a further embodiment of the present invention wherein the valve has a unitary housing.

FIG. 15 illustrates an embodiment of the valve 1 having a unitary housing 21.

Figure 16:
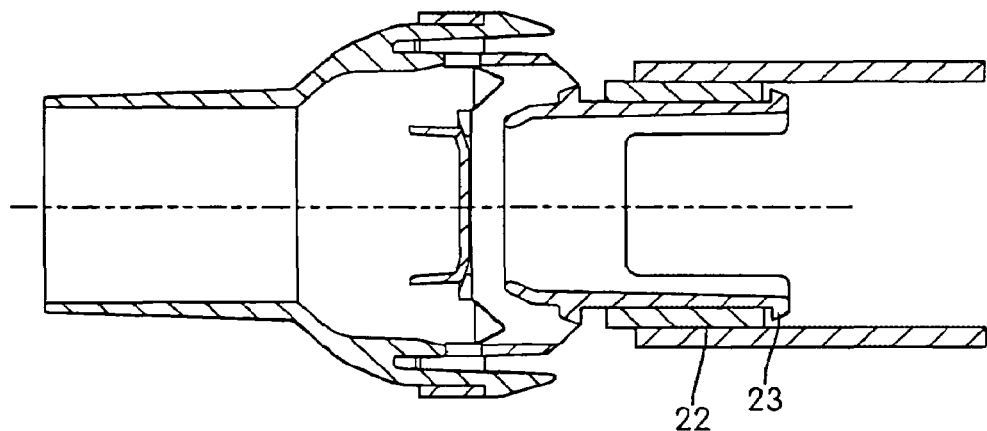
FIG. 16 is a cross sectional view of a yet further embodiment of the present invention wherein the valve includes a swivel conduit connector.

FIG. 16 illustrates another embodiment of the valve 1 with a snap on swivel connector 22 that engages over resilient fingers 23. This embodiment obviates the need for a separate swivel connector elsewhere in the, gas supply circuit.

In another embodiment (not shown) the swivel connection 23 is used in conjunction with the unitary housing 21.

Figure 17:
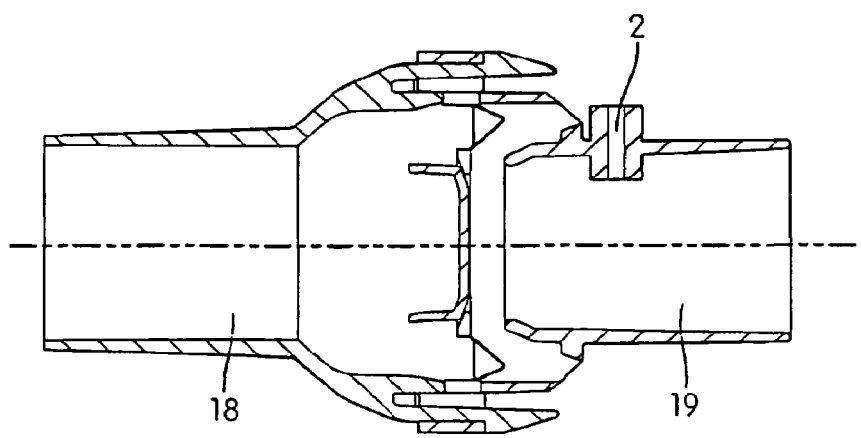
FIG. 17 is a cross sectional view of a yet further embodiment of the present invention wherein the valve includes an oxygen injection point.

FIG. 17 shows an embodiment of the valve 1 with an oxygen injection point 2 cast into the downstream housing 7.

In another embodiment (not shown) the oxygen injection point 2 is cast into the unitary housing. The oxygen injection point can also be used in conjunction with a snap-on swivel connector.

FIG. 18 shows an embodiment of the flap 13 which includes an external rim 24 of stepped cross section which assists in locating the flap 13 in the housing(s). The rim 24 is received within a corresponding recess 24.1 (see, e.g., FIG. 15) in the housing to facilitate locating and mounting the flap 13 in the housing.

FIG. 19 shows another embodiment of the flap 13 having an external rim 25 of rectangular cross section.

FIG. 20 shows yet another embodiment of the flap 13 having a substantially cylindrical formation 26 between the flaps and the rim 27. The cylindrical formation 26 and the rim 27 facilitates locating the flap correctly within the housing.

FIG. 21 shows an embodiment of the flap 13 with a circular shaped cross section of the toroid 28. FIG. 21.1 shows a flap 13 having a seal in the form of a full or part ellipse 33.

FIG. 22 shows an embodiment of the flap 13 with a triangular shaped cross section of the toroid 29.

Figure 23:
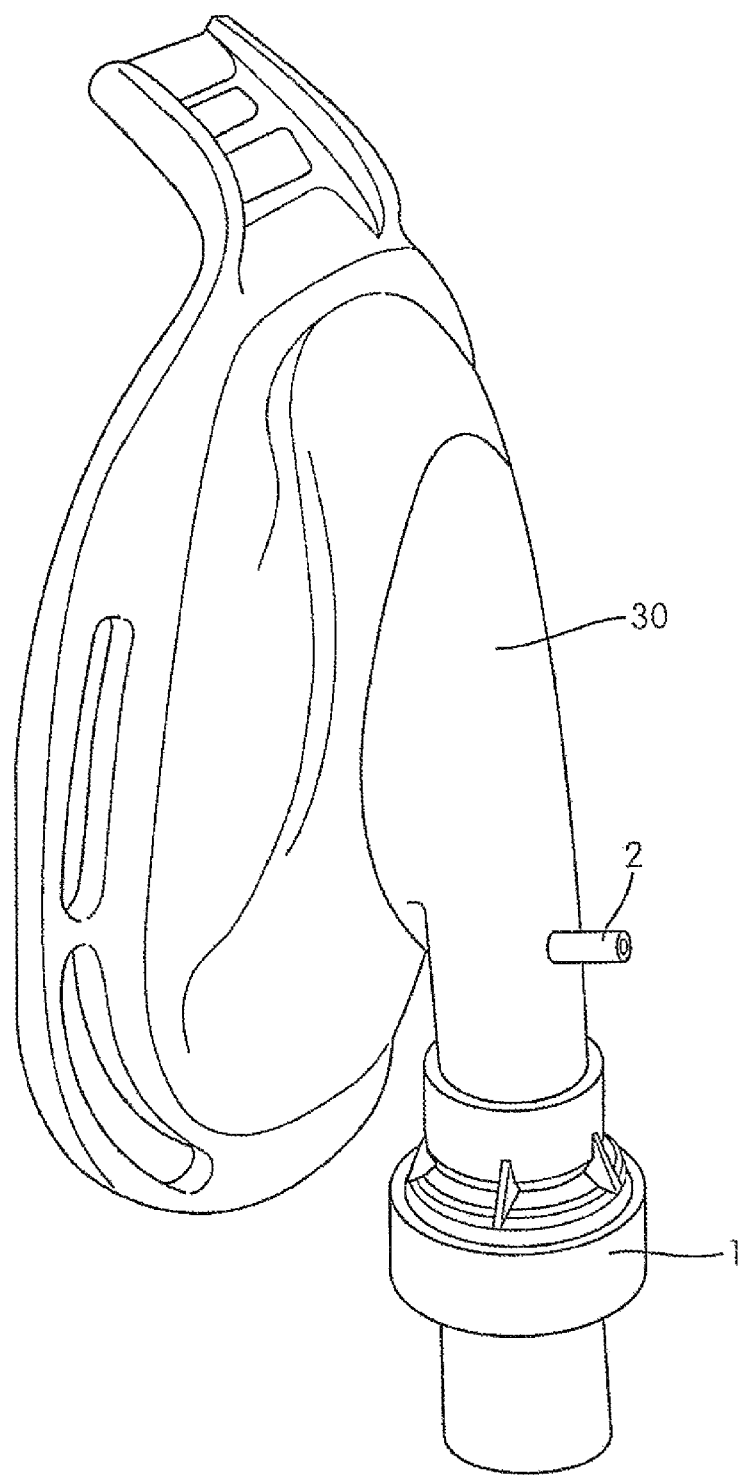
FIG. 23 is a perspective view of an alternative embodiment of the present invention wherein the valve is attached to a mask.

FIG. 23 illustrates an embodiment of the valve 1 in which the valve is attached to a face mask 30 with an oxygen injection point 2.

Figure 24:
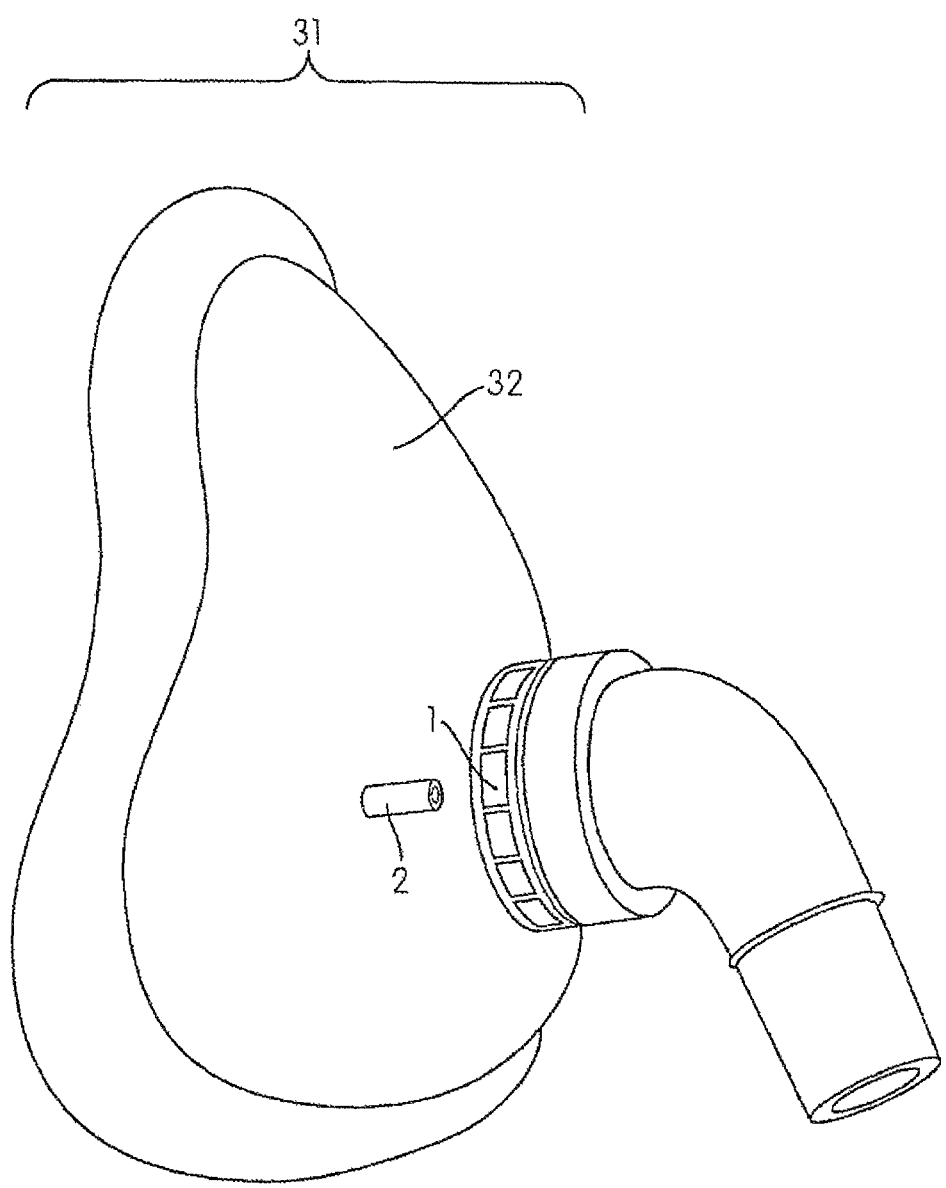
FIG. 24 is a perspective view of another embodiment of the present invention wherein the valve is integral with a mask.

FIG. 24 illustrates a further embodiment of the valve 1 incorporated into a mask 31 with an oxygen injection point 2. In this embodiment, the valve 1 is integrally formed with the mask shell 32 thereby obviating the push-on connection between the mask 31 and the valve 1.

The valve according to the present invention can be used for any type of air delivery system, it is preferably used in CPAP applications for the treatment of OSA or Non-Invasive Positive Pressure Ventilation (NIPPV).

Preferred embodiments of the valve of the present invention have the advantage of being able to operate independent of orientation. That is, although the valve has to be connected in the right direction between the flow generator and the mask, it can be inverted, held sideways, etc. which often occurs during the time when the patient sleeps.

Another advantage of the valve of the present invention is it has only one moving or flexing part providing consistent operation. Further, the valve can be disassembled cleaned and reassembled very easily at home or at a hospital or clinic due to it having fewer parts. The valve of the present invention is also very quiet in operation.

Although the invention has been described with reference to specific examples, it will be appreciated by those skilled in the art that the invention may be embodied in many other forms. In particular, a valve of the present invention may be constructed of components which have dimensions, configurations and mechanical properties (including the mechanical properties of the flap assembly) that vary from those of the disclosed embodiments. Such valves can have operating thresholds different from valve embodiments which achieved a closure at 2 cm $H_2O$. The actual dimensions, configurations and mechanical properties will be chosen to achieve a valve having performance characteristic including operating threshold that will meet the specific needs of the chosen application.

The foregoing description of the embodiments of the present invention provides illustration and description, but is not intended to be exhaustive or to limit the invention to the precise form disclosed. Modifications and variations are possible consistent with the above teachings or may be acquired from practice of the invention without departing from the spirit and scope of the invention.

What is claimed is:

1. A respiratory mask system for treatment of a patient having a breathing disorder, the mask system comprising:
    a mask having a mask cushion to contact a patient's face, and a shell coupled to the mask cushion, the mask at least partially forming a cavity for receiving breathable gas in a pressure range suitable for treatment of sleep apnea while the patient is sleeping;
    headgear configured to maintain the mask in a position on a patient's head in use; and
    a vent assembly to allow gas to exhaust to ambient atmosphere, the vent assembly having:
        a first vent portion being open to the ambient atmosphere and being disposed a first distance from the cavity, and
        a second vent portion being open to the ambient atmosphere and being disposed a second distance from the cavity,
        wherein the first and second vent portions are always open to the ambient atmosphere,
        wherein the first distance from the cavity to the ambient atmosphere through the first vent portion is shorter than the second distance from the cavity to the ambient atmosphere through the second vent portion, and
        wherein a first airflow through the first vent portion is greater than a second airflow through the second vent portion when the first vent portion and the second vent portion are open to the ambient atmosphere at the same time.

2. The respiratory mask system of claim 1, wherein the first distance is a first airflow path distance and the second distance is a second airflow path distance.

3. The respiratory mask system of claim 1, wherein, in use of the mask system, a total combined airflow through the first vent portion and the second vent portion remains substantially constant over time.

4. The respiratory mask system of claim 1, wherein, in use of the mask system, carbon dioxide exhaled by the patient is exhausted out of the cavity through the first vent portion and/or the second vent portion.

5. The respiratory mask system of claim 1, wherein the mask is a nasal only mask, a nose-mouth mask, a full-face mask, nasal prongs, or nasal pillows.

6. The respiratory mask system of claim 1, further comprising an anti-asphyxia valve, wherein a position of the anti-asphyxia valve does not prevent airflow through the first vent portion and does not prevent airflow through the second vent portion when breathable gas is delivered to the cavity in the pressure range suitable for treatment of sleep apnea.

7. The respiratory mask system of claim 1, wherein the second vent portion includes more than one opening.

8. The respiratory mask system of claim 1, wherein the first vent portion and the second vent portion have different sizes.

9. The respiratory mask system of claim 1, wherein at a first point in time, a first non-zero volumetric flow rate from the cavity to the ambient atmosphere through the first vent portion is greater than a second non-zero volumetric flow rate from the cavity to the ambient atmosphere through the second vent portion.

10. The respiratory mask system of claim 1, further comprising an air inlet in fluid communication with the cavity and configured to receive the breathable gas, and an elbow extending from the air inlet and adapted to connect to an air delivery conduit coupled to a flow generator.

11. The respiratory mask system of claim 10, wherein the second vent portion is positioned adjacent to the air inlet.

12. The respiratory mask system of claim 1, wherein a time t1 for the gas in the cavity to exhaust through the first vent portion is less than a time t2 for the gas in the cavity to exhaust from second vent portion.

13. The respiratory mask system of claim 1, wherein the first vent portion is an orifice through the mask.

14. The respiratory mask system of claim 1, wherein the volume of the mask remains substantially constant while in use.

15. The respiratory mask system of claim 1, wherein the headgear is configured to maintain the vent assembly in a position on a patient's head in use.

16. The respiratory mask system of claim 1, wherein the headgear is coupled to the shell.

17. The respiratory mask system of claim 1, wherein:
    the mask is a nose and mouth mask and is configured to deliver the breathable gas to a nose and a mouth of the patient;
    the first vent portion and the second vent portion are configured to provide continuous communication between the ambient atmosphere and the cavity;
    an anti-asphyxia valve is coupled to the mask and a position of the anti-asphyxia valve does not prevent airflow through the first vent portion and does not prevent airflow through the second vent portion when the breathable gas is delivered;
an air inlet is in fluid communication with the cavity and is configured to receive the breathable gas, and an elbow extends from the air inlet and is adapted to connect to an air delivery conduit coupled to a flow generator, the second vent portion is positioned adjacent to the air inlet; and
in use of the mask system, carbon dioxide exhaled by the patient is exhausted out of the cavity through the first vent portion and/or the second vent portion.

18. The respiratory mask system of claim 1, wherein:
the mask is a nasal only mask;
the first vent portion and the second vent portion are configured to provide continuous communication between the ambient atmosphere and the cavity;
the first vent portion is disposed proximate to the patient's nose;
an air inlet is in fluid communication with the cavity and is configured to receive the breathable gas, and an elbow extends from the air inlet and is adapted to connect to an air delivery conduit coupled to a flow generator, the second vent portion is positioned adjacent to the air inlet; and
in use of the mask system, carbon dioxide exhaled by the patient is exhausted out of the cavity through the first vent portion and/or the second vent portion.

19. The respiratory mask system of claim 1, wherein:
nasal pillows are the mask;
the first vent portion and the second vent portion are configured to provide continuous communication between the ambient atmosphere and the cavity;
the first vent portion is disposed proximate to the patient's nose;
an air inlet is in fluid communication with the cavity and is configured to receive the breathable gas, and an elbow extends from the air inlet and is adapted to connect to an air delivery conduit coupled to a flow generator, the second vent portion is positioned adjacent to the air inlet; and
in use of the mask system, carbon dioxide exhaled by the patient is exhausted out of the cavity through the first vent portion and/or the second vent portion.

20. A system comprising:
the respiratory mask system of claim 1;
a flow generator configured to output a pressurized fluid; and
a conduit connected to the mask and the flow generator, the conduit transporting the pressurized fluid from the flow generator to the cavity.

21. The system of claim 20, further comprising an elbow inserted into an inlet of the respiratory mask system, the conduit including a first end coupled to the elbow and a second end coupled to the flow generator.

22. A respiratory mask system for treatment of a patient having a breathing disorder, the mask system comprising:
a mask having a mask cushion to contact a patient's face, and a shell coupled to the mask cushion, the mask at least partially forming a cavity for receiving breathable gas in a pressure range suitable for treatment of sleep apnea while the patient is sleeping;
headgear configured to maintain the mask in a position on a patient's head in use; and
a vent assembly to allow gas to exhaust to atmosphere, the vent assembly having a first vent portion, and a second vent portion spaced apart from the first vent portion, wherein the first vent portion and the second vent portion are always open, and provide continuous communication between the atmosphere and the cavity;
wherein, in use of the mask system:
a total combined airflow through the first vent portion and the second vent portion remains substantially constant over time, and
airflow through the first vent portion is greater than airflow through the second vent portion at a first point in time.

23. A respiratory mask system for treatment of a patient having a breathing disorder, the mask system comprising:
a mask having a mask cushion to contact a patient's face, and a shell coupled to the mask cushion, the mask at least partially forming a cavity for receiving breathable gas in a pressure range suitable for treatment of sleep apnea while the patient is sleeping;
headgear configured to maintain the mask in a position on a patient's head in use; and
a vent assembly to allow gas to exhaust to atmosphere, the vent assembly having a first vent portion, and a second vent portion spaced apart from the first vent portion,
wherein, in use of the mask system:
a total combined airflow through the first vent portion and the second vent portion remains substantially constant over time, and
airflow through the first vent portion is greater than airflow through the second vent portion at a first point in time, wherein airflow through the first vent portion further increases while airflow through the second vent portion decreases when there is an obstruction in a flow path through the second vent portion.

24. The respiratory mask system of claim 22, wherein a ratio of airflow through the first vent portion compared to the second vent portion is variable over time.

25. The respiratory mask system of claim 22, further comprising a plurality of holes configured to allow exhaled gas to pass in order to exit the mask through the first vent portion.

26. The respiratory mask system of claim 22, wherein a first exhale distance to atmosphere from the cavity to the first vent portion is less than a second exhale distance to atmosphere from the cavity to the second vent portion.

27. The respiratory mask system of claim 22, wherein exhaled air is the gas exhausted through the first vent portion and the second vent portion.

28. The respiratory mask system of claim 22, wherein the mask is a nasal mask, a nose-mouth mask, a full-face mask, nasal prongs, or nasal pillows.

29. The respiratory mask system of claim 22, wherein a first distance from the cavity to ambient atmosphere through the first vent portion is shorter than a second distance from the cavity to the ambient atmosphere through the second vent portion.

30. A system comprising:
the respiratory mask system of claim 22;
a flow generator configured to output a pressurized fluid; and
a conduit connected to the respiratory mask and the flow generator, the conduit transporting the pressurized fluid from the flow generator to the cavity.

* * * * *